(12) United States Patent
Sim et al.

(10) Patent No.: US 8,586,580 B2
(45) Date of Patent: Nov. 19, 2013

(54) 2,7-SUBSTITUTED THIENO[3,2-D] PYRIMIDINE COMPOUNDS AS PROTEIN KINASE INHIBITORS

(75) Inventors: Tae Bo Sim, Seoul (KR); Hwan Geun Choi, Seoul (KR); Jung Mi Hah, Seoul (KR); Young Jin Ham, Seoul (KR); Eun Jin Jun, Seoul (KR); Jung Hun Lee, Busan (KR); Hwan Kim, Gyeonggi-do (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/503,125

(22) PCT Filed: Oct. 15, 2010

(86) PCT No.: PCT/KR2010/007093
§ 371 (c)(1),
(2), (4) Date: Jul. 11, 2012

(87) PCT Pub. No.: WO2011/049332
PCT Pub. Date: Apr. 28, 2011

(65) Prior Publication Data
US 2012/0277424 A1    Nov. 1, 2012

(30) Foreign Application Priority Data

Oct. 22, 2009    (KR) .................. 10-2009-0100867

(51) Int. Cl.
C07D 495/04    (2006.01)
C07D 495/02    (2006.01)
A61K 31/505    (2006.01)
A61P 35/00    (2006.01)

(52) U.S. Cl.
USPC .................. 514/232.5; 514/234.2; 514/260.1; 544/117; 544/278

(58) Field of Classification Search
USPC .......... 544/117, 278; 514/232.5, 234.2, 260.1
See application file for complete search history.

(56) References Cited

U.S. PATENT DOCUMENTS

| 2006/0004002 A1 | 1/2006 | Thrash et al. |
| 2007/0275984 A1 | 11/2007 | Imogai et al. |
| 2009/0098086 A1 | 4/2009 | Zask et al. |
| 2009/0192176 A1 | 7/2009 | Zask et al. |

OTHER PUBLICATIONS

Adrian J. Folkes et al., "The Identification of 2-(1H-Indazol-4-yl)-6-(4-methanesulfonyl-piperazin-1-ylmethyl)-4-morpholin-4-yl-thieno[3,2-d]pyrimidine (GDC-0941) as a Potent, Selective, Orally Bioavailable Inhibitor of Class I PI3 Kinase for the Treatment of Cancer", J. Med. Chem., vol. 51, No. 18, Aug. 2008, pp. 5522-5532.
Francis X. Tavares et al., "6-(4-Chlorophenyl)-3-substituted-thieno[3,2-d]pyrimidin-4(3H)-one-Based Melanin-Concentrating Hormone Receptor 1 Antagonist", J. Med. Chem., vol. 49, No. 24, Nov. 2006, pp. 7108-7118.
Tara R. Rheault et al., "Thienopyrimidine-based dual EGFR/ErbB-2 inhibitors", Bioorganic Medicinal Chemistry Letters, vol. 19, 2009, pp. 817-820.
G. Manning et al., "The Protein Kinase Complement of the Human Genome", Science, vol. 298, Dec. 2002, pp. 1912-1934.
Elizabeth A. Beierle et al., "TAE226 Inhibits Human Neuroblastoma Cell Survival", Cancer Investigations, vol. 26, 2008, pp. 145-151.
Jyotsnabaran Halder et al., "Therapeutic Efficacy of a Novel Focal Adhesion Kinase Inhibitor TAE226 in Ovarian Carcinoma", Cancer Research, vol. 67, Nov. 2007, pp. 10976-10983.
Jill K. Slack-Davis et al., "Cellular characterization of FAK family kinase inhibitors", Cellular and Molecular Biology, vol. 69, abstract only, (2006).
S. Roelle et al., "Essential role of Pyk2 and Src kinase activation in neuropeptide-induced proliferation of small cell lung cancer cells", Oncogene, vol. 27, 2008, pp. 1737-1748.
T-C Yuan et al., "ErbB-2 via PYK2 upregulates the adhesive ability of androgen receptor-positive human prostate cancer cells", Oncogene, vol. 26, 2007, pp. 7552-7559.
CK Sun et al., "The significance of proline-rich tyrosine kinase2 (Pyk2) on hepatocellular carcinoma progression and recurrence", British Journal of Cancer, vol. 97, 2007, pp. 50-57.
Christopher A. Lipinski et al., "The Tyrosine Kinase Pyk2 Promotes Migration and Invasion of Glioma Cells", Neolasia, vol. 7, No. 5, May 2005, pp. 435-445.
Michael S. Lyons, et al., "Isolation of the Zebrafish Homologues for the *tie*-1 and *tie*-2 Endothelium-Specific Receptor Tyrosine Kinases", Developmental Dynamics, vol. 212, 1998, pp. 133-140.
KG Peters et al., "Expression of Tie2/Tek in breast tumor vasculature provides a new marker for evaluation of tumor angiogenesis", British Journal of Cancer, vol. 77, No. 1, 1998, pp. 51-56.
Nina Jones et al., "Identification of Tek/Tie2 Binding Partners", The Journal of Biological Chemistry, vol. 274, No. 43, Oct. 1999, pp. 30896-30905.

*Primary Examiner* — Bruck Kifle
(74) *Attorney, Agent, or Firm* — Staas & Halsey LLP

(57) ABSTRACT

Disclosed are a 2,7-substituted thieno[3,2-d]pyrimidine compound having a protein kinase inhibition activity, a pharmaceutically acceptable salt, and a pharmaceutical composition for prevention and treatment of diseases caused by abnormal cell growth comprising the compound as an effective ingredient.

Since the novel 2,7-substituted thieno[3,2-d]pyrimidine compound exhibits superior inhibition activity against various protein kinases involved in growth factor signal transduction, it is useful as an agent for preventing or treating diseases caused by abnormal cell growth.

7 Claims, No Drawings

2,7-SUBSTITUTED THIENO[3,2-D] PYRIMIDINE COMPOUNDS AS PROTEIN KINASE INHIBITORS

CROSS REFERENCE TO RELATED APPLICATIONS

This application claims the benefit of International Application No. PCT/KR2010/0070936, filed Oct. 15, 2010, and claims the benefit of Korean Application No. 10-2009-0100867, filed Oct. 22, 2009, the disclosures of all of which are incorporated herein by reference.

TECHNICAL FIELD

The present invention relates to a 2,7-substituted thieno[3,2-d]pyrimidine compound having a protein kinase inhibition activity, a pharmaceutically acceptable salt, and a pharmaceutical composition for prevention and treatment of diseases caused by abnormal cell growth including the compound as an effective ingredient.

BACKGROUND ART

A protein kinase is an enzyme which catalyzes phosphorylation of hydroxyl groups on tyrosine, serine and threonine residues of proteins. It plays an important role in signal transduction of growth factors involved in growth, differentiation and proliferation of cells.

To maintain homeostasis, it is necessary to keep good balance in turning on and off of the signal transduction system. However, mutation or overexpression of specific protein kinases disrupts the signal transduction system in normal cells and causes various diseases including cancers, inflammations, metabolic diseases, brain diseases, or the like. Typical protein kinases that lead to diseases caused by abnormal cell growth include Raf, KDR, Fms, Tie2, SAPK2a, Ret, Abl, Abl (T315I), ALK, Aurora A, Bmx, CDK/cyclinE, Kit, Src, EGFR, EphA1, FGFR3, Flt3, Fms, IGF-1R, IKKb, IR, Itk, JAK2, KDR, Met, mTOR, PDGFRa, Plk1, Ret, Syk, Tie2, TrtB, etc.

It is estimated that there are 518 different kinds of protein kinase genes in humans constituting about 1.7% of the entire human genes [Manning et al., *Science*, 2002, 298, 1912]. Human protein kinases are largely divided into (90 or more) tyrosine-specific protein kinases and serine/threonine-specific protein kinase. The tyrosine-specific protein kinases may be divided into 58 receptor tyrosine kinases, which are grouped into 20 subfamilies, and 32 cytoplasmic/non-receptor tyrosine kinases, which are grouped into 10 subfamilies. The receptor tyrosine kinase has an extracellular domain capable of binding to a growth factor and a cytoplasmic active site that can phosphorylate the tyrosine residue. When a growth factor binds at the extracellular growth factor receptor site of the receptor tyrosine kinase, the receptor tyrosine kinase forms a dimer and the tyrosine residues in the cytoplasm are autophosphorylated. Then, the downstream proteins are sequentially phosphorylated, and as the signal transduction proceeds in the nucleus, the transcription factors that induce cancer are overexpressed in the end.

Focal adhesion kinase (FAK) is a 125 kD tyrosine-specific protein kinase present in cytoplasm. FAK plays a critical role in migration, proliferation and survival of cells by regulating the signal transduction system of integrin and growth factors. FAK protein and FAK mRNA were found to be overexpressed/activated in various cancer cells, including squamous cell carcinoma, invasive rectal cancer/breast cancer, metastatic prostate cancer, melanoma and glioma. Novartis' FAK inhibitor TAE226 [*Cancer Invest.* 2008, 26(2), 145] was proven to be effective for breast cancer through three animal models (HeyA8, SKOV3ip1 and HeyA8-MDR) [*Cancer Res.* 2007, 67(22), 10976)]. And, Pfizer's FAK inhibitor PF-573, 228 [*Proc. Am. Assoc. Cancer Res.*, 2006, 47, Abst. 5072] is successfully under clinical trial. It was shown effective for prostate cancer (PC-3M), breast cancer (BT474), pancreatic cancer (BxPc3), lung cancer (H460) and brain cancer (U87MG) through animal models. In addition, a concurrent administration of FAK inhibitor (TAE226) and docetaxel showed an excellent efficiency (85-97% tumor reduction, P values <0.01) in an animal model [*Cancer Res.* 2007, 67(22), 10976].

FAK participates in the signaling of integrin. When integrin receptors cluster in response to various stimulations from outside, the cytoplasmic domain (cytoplasmic tail) of integrin binds to the cytoskeleton and signaling proteins. The FERM (4.1 protein/ezrin/radixin/moesin) domain and the FAT (focal adhesion targeting) domain of FAK independently bind with the cytoplasmic domain of integrin and allow the FAK to be located at the focal adhesion site. The FAKs clustered close to the focal adhesion site are activated via intramolecular or intermolecular phosphorylation of the Y397 residue. Then, the SH2 domain of Src kinase binds to the phosphorylated Y397 residue of FAK to form an FAK/Src complex. The Src kinase bound to FAK further phosphorylates other tyrosine residues (Y407, Y576/577, Y861 and Y925) of FAK. Also, the FAK/Src complex binds to various signaling proteins (P130Cas, Grb2, PI3K and Grb7) and mediates phosphorylation. In normal cells, the signal transduction through FAK is mediated under strict regulation. However, in tumorized cells, FAK is overexpressed and activated thereby exhibiting various features of malignant tumors. FAK facilitates proliferation of cancer cells, increases invasion, and migration of cancer cells. Further, FAK is also known to suppress cancer cell apoptosis and increase angiogenesis.

FAK is a protein targeted by many growth factor receptors including epidermal growth factor receptor (EGFR) and platelet-derived growth factor receptor (PDGFR), as well as integrin. Overexpression of the receptors or expression of activated receptors converts normal cells into tumor cells. Thus, FAK is an important kinase involved in tumor-related signal transduction of the receptors. It has been reported that the N-terminal FERM domain of FAK binds to EGFR and the C-terminal domain of FAK is involved in the cell migration mediated by epidermal growth factor (EGF). That is, FAK recognizes the signal from the EGFR receptor through the N-terminal FERM domain and recognizes the signal from the integrin through the C-terminal FAT domain, and thereby integrates signals from the outside of the cell.

Apoptosis may be induced by inhibiting FAK in various manners. Cell survival mediated by FAK is mainly conducted by phosphoinositide 3-kinase (PI 3-kinase). The phosphorylated Y397 site of FAK binds to PI 3-kinase and synthesizes PI(3,4,5)P3 and PI(3,4)P2 as second messengers, which move protein kinase B (PKB, also called Ala) to the cell membrane so that it can be phosphorylated by 3'-phosphoinositide-dependent kinase (PDK). Thus activated PKB deactivates apoptotic proteins (e.g., p21WAF, FKHR, Bad and GSK-3) and, thereby inhibits apoptosis. Another signal for survival is the binding of the SH3 domain of p130Cas to the proline-rich motif of FAK, whereby phosphorylation of the tyrosine residues of p130Cas is induced by FAK/Src and Ras is activated.

The role of FAK in the cell cycle is explained as follows. If the Y925 site is phosphorylated, FAK binds to growth factor receptor-bound protein 2 (Grb2) thereby activating the Ras/Erk pathway. Overexpression of FAK facilitates G1 to S phase transition, and expression of FAK related non-kinase (FRNK), an inhibitor of FAK, inhibits the expression of cyclin D1 and induces the expression of the CDK inhibitor p21, thereby delaying the progress of the cell cycle. However, overexpression of cyclin D1 rescues the cells from the cell cycle arrest by FRNK.

The only subtype of FAK, proline-rich tyrosine kinase 2 (PYK2), is the most highly distributed in nerve cells. Recently, it is reported as a useful molecular target in the development of anticancer drugs for small-cell lung cancer [*Oncogene.* 2008, 27(12), 1737], prostate cancer [*Oncogene.* 2007, 26(54), 7552], liver cell carcinoma [*Br. J. Cancer.* 2007, 97(1), 50] and glioma [*Neoplasia.* 2005, 7(5), 435].

FAK comprises four domains: 1) the 4.1 protein/ezrin/radixin/moesin (FERM) domain is an amino-terminal domain that interacts with integrin receptor, platelet-derived growth factor receptor (PDGFR), epidermal growth factor receptor (EGFR), etc., and inhibits kinase activity through direct interaction with the kinase domain; 2) the kinase domain; 3) three proline-rich (PR) regions; and 4) the focal adhesion targeting (FAT) domain situated at the carboxyl-terminal interacts with paxillin, talin, p190RhoGEF, RhoA-specific GDP/GTP exchange factor, etc. The alternative splicing product of FAK, FAK-related non-kinase domain (FRNK), consists of PR1, PR2 and FAT domains and acts as an antagonistic regulatory factor of FAK.

For FAK to be activated, autophosphorylation of Y397 located at the junction of the FERM and kinase domains is required. Src kinase binds to the phosphorylated Y397 and sequentially phosphorylates Y576 and 577. When Y925 is phosphorylated in the end, the signal transduction of FAK is turned on through Grb2. The FAK inhibitors currently under development are shown to inhibit the autophosphorylation of Y397 by targeting the ATP binding site of the kinase domain. The extent of the inhibition of Y397 autophosphorylation is an important measure (biomarker) in the efficiency test using an animal model.

The progress that has been made in the development of low molecular weight FAK inhibitors is as follows. Of the 26 lead compounds that have been proposed for the FAK inhibitors, only the Pfizer's PF-562271 is under clinical trial phase I at present. PF-562271 is an ATP-competitive FAK inhibitor ($IC_{50}$=1.5 nM) and a homologous Pyk2 inhibitor (13 nM). It inhibits autophosphorylation at the FAK Y397 site in fibroblasts, epithelial cells and cancer cells. Further, it inhibits the migration of most cancer cells, but does not affect the growth of normal cells. No special toxicity has been observed and inhibition of tumor growth or tumor degeneration by 42-90% was observed in in vivo human tumor xenograft tests (25-100 mg/kg p.o.) for prostate cancer PC-3, breast cancer BT-474, colon LoVo, lung cancer NCI-H460, glioblastoma U-87 MG and pancreatic cancer BxPC-3 cells.

Vascular endothelial growth factor receptors (VEGFRs) are receptor tyrosine kinases (RTKs) and important regulatory factors of angiogenesis. They are involved in the formation of blood vessels and lymphatic vessels and in homeostasis, and exert important effects on nerve cell. Vascular endothelial growth factor (VEGF) is produced mostly by vascular endothelial cells, hematopoietic cells and stromal cells under a hypoxic condition or by stimulations from growth factors such as TGF, interleukin and PDGF. VEGF binds to VEGFR-1, -2 and -3. Each VEGF isoform binds to a specific receptor, thereby inducing the formation of a receptor homozygote or heterozygote, and activates each signal transduction system. The signal specificity of VEGFR is further fine-tuned by co-receptors such as neuropilin, heparan sulfate, integrin, cadherin, etc.

The biological function of VEGF is mediated by type III RTK, VEGFR-1 (Flt-1), VEGFR-2 (KDR/Flk-1) and VEGFR-3 (Flt-4). VEGFR is closely related to Fms, Kit and PDGFR. Each VEGF binds to specific receptors. VEGF-A binds to VEGFR-1, -2 and receptor zygote, whereas VEGF-C binds to VEGFR-2, -3. PIGF and VEGF-B interact exclusively with VEGFR-1, and VEGF-E interacts only with VEGFR-2. VEGF-F interacts with VEGFR-1 or -2. Whereas VEGF-A, -B and PIGF are preferentially required for the formation of blood vessels, VEGF-C and -D are essential in the formation of lymphatic vessels. Angiogenesis is essential in the proliferation and transition of tumors, since it supplies nutrients and oxygen to the tumors and provides channels for transition to cancer cells. Normally, angiogenesis is balanced by angiogenic stimulators and angiogenic inhibitors. If the balance is broken, as in cancer cells, the growth factor that affects the vascular endothelial cells most, i.e., VEGF, activates its receptor, VEGFR. At present, various researches are under way on the inhibitors that inhibit the receptor tyrosine kinase of VEGF using low molecular weight synthetic substances, which are advantageous in that they are applicable also to solid tumors and have fewer side effects because they inhibit angiogenesis in the cancer cells only.

Tie2 is a kind of receptor tyrosine kinase and is deeply involved with angiogenesis and vasculature. The domain structure of Tie2 is very highly conserved in all vertebrates [Lyons et al., 1998]. The ligand of Tie2 is angiopoietin (Ang). Ang2 does not induce autophosphorylation of Tie2, but interferes with the activation of Tie2 by Ang1. In endothelial cells, the activation of Tie2 by Ang2 induces activation of PI3K-Akt [Jones et al., 1999]. In the mitogen-activated protein kinase (MAPK) signal transduction pathway, which is the main signal transduction system of Tie2, the adaptor protein GRB2 and the protein tyrosine phosphatase SHP2 play a key role in dimerization of the Tie2 receptor tyrosine kinase through autophosphorylation. Ang/Tie2 and the VEGF signal transduction pathway are important in angiogenesis of cancer cells. Tie2 is expressed in vascular endothelial cells. Especially, the expression increases remarkably at the site invaded by cancer cell. Overexpression of Tie2 was observed in breast cancer [Peters et al., 1998] and also in uterine cancer, liver cancer and brain cancer.

Several compounds with the thieno[3,2-d]pyrimidine structure have been synthesized. However, the substituted thieno[3,2-d]pyrimidine compound of the present invention with specific substituents at the 2- and 7-positions of thieno [3,2-d]pyrimidine is a novel compound not disclosed in any literature. Moreover, the inhibition activity against various protein kinases or the possibility of the substituted thieno[3,2-d]pyrimidine compound with the specific substituents at the 2- and 7-positions has not been predicted in any literature.

DISCLOSURE

Technical Problem

An object of the present invention is to provide a novel 2,7-substituted thieno[3,2-d]pyrimidine compound having specific substituents at the 2- and 7-positions of thieno[3,2-d]pyrimidine or a pharmaceutically acceptable salt thereof.

Another object of the present invention is to provide a pharmaceutical composition for prevention and treatment of diseases caused by abnormal cell growth comprising the novel 2,7-substituted thieno[3,2-d]pyrimidine compound or a pharmaceutically acceptable salt thereof as an effective ingredient.

Technical Solution

The present invention provides a 2,7-substituted thieno[3,2-d]pyrimidine compound represented by Chemical Formula 1, a pharmaceutically acceptable salt thereof, a hydrate thereof or a solvate thereof:

[Chemical Formula 1]

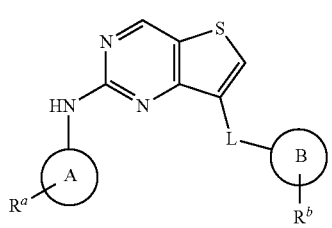

wherein

A represents 5- to 14-membered heteroaryl containing 1 to 4 heteroatom(s) selected from nitrogen, oxygen and sulfur atoms;

$R^a$ represents hydrogen, halogen, oxo (=O), $C_1$-$C_6$ alkyl, $C_1$-$C_6$ alkoxy, $C_1$-$C_6$ alkylcarbonyl, $C_1$-$C_6$ alkoxycarbonyl, amino $C_1$-$C_6$ alkoxy, mono($C_1$-$C_6$ alkyl)amino $C_1$-$C_6$ alkoxy, di($C_1$-$C_6$ alkyl)amino $C_1$-$C_6$ alkoxy, substituted or unsubstituted heterocycle, or substituted or unsubstituted phenyl;

L is nonexistent or represents —NH— or —N($C_1$-$C_6$ alkyl)-;

B represents phenyl or 5- to 14-membered single or fused heteroaryl containing 1 to 4 heteroatom(s) selected from nitrogen, oxygen and sulfur atoms;

$R^b$ represents hydrogen, nitro, amino, hydroxy, $C_1$-$C_6$ haloalkyl, $C_1$-$C_6$ alkoxy, —$(CH_2)_n$—$R^1$, —$C(O)OR^2$, —$C(O)NR^3R^4$, —$NR^2C(O)R^3$, —$NR^2C(O)NR^3R^4$, —$SO_2NR^3R^4$ or —$NR^2SO_2R^3$;

n represents an integer from 0 to 3;

$R^1$ represents hydrogen, $C_1$-$C_6$ alkyl, haloalkyl, hydroxy, methanesulfonyl, phenyl, or substituted or unsubstituted heterocycle;

$R^2$ represents hydrogen or $C_1$-$C_6$ alkyl;

$R^3$ and $R^4$, which are the same or different, represent hydrogen, $C_1$-$C_6$ alkyl, $C_3$-$C_6$ cycloalkyl, $C_1$-$C_6$ haloalkyl, or substituted or unsubstituted phenyl;

the substituted phenyl is substituted with a substituent selected from halogen, $C_1$-$C_6$ haloalkyl, carboxyl and $C_1$-$C_6$ alkoxycarbonyl; and the substituted heterocycle represents morpholino, piperidinyl or piperazinyl substituted with a substituent selected from $C_1$-$C_6$ alkyl and $C_1$-$C_6$ hydroxyalkyl.

Advantageous Effects

The 2,7-substituted thieno[3,2-d]pyrimidine compound represented by Chemical Formula 1, a pharmaceutically acceptable salt thereof, a hydrate thereof or a solvate thereof has superior capability of inhibiting the activity of protein kinases selected from ALK, Aurora A, EphA1, FAK, Flt3, Fms, Itk, KDR, Kit, Met, Ret, Src, Syk, Tie2 and TrkB, and is effective for preventing and treating diseases caused by abnormal cell growth.

Specifically, the diseases caused by abnormal cell growth that may be prevented or treated by the compound according to the present invention may include various tumors selected from stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma, fibroadenoma, etc.

BEST MODE

Hereinafter, the embodiments of the present invention will be described in detail.

A pharmaceutically acceptable salt of the 2,7-substituted thieno[3,2-d]pyrimidine compound represented by Chemical Formula 1 may be prepared by a method commonly employed in the art. The pharmaceutically acceptable salt should be less toxic to the human body and should not have negative effects on the biological activity and physical and chemical properties of the mother compound. The pharmaceutically acceptable salt includes a free acid, an acid addition salt of a base compound represented by Chemical Formula 1, an alkali metal salt (e.g., a sodium salt), an alkaline earth metal salt (e.g., a calcium salt), an organic salt, an organic base addition salt of a carboxylic acid represented by Chemical Formula 1, and an amino acid addition salt. The free acid that may be used to prepare the pharmaceutically acceptable salt includes an inorganic acid or an organic acid. The inorganic acid may be hydrochloric acid, sulfuric acid, nitric acid, phosphoric acid, perchloric acid, bromic acid, or the like. The organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, or the like. The organic base that may be used to prepare the organic base addition salt includes tris (hydroxymethyl)methylamine, dicyclohexylamine, etc. The amino acid that may be used to prepare the amino acid addition salt includes a naturally occurring amino acid such as alanine, glycine, etc.

The 2,7-substituted thieno[3,2-d]pyrimidine compound represented by Chemical Formula 1 includes, in addition to the pharmaceutically acceptable salts, all hydrates and solvates. The hydrate or the solvate may be prepared by dissolving the 2,7-substituted thieno[3,2-d]pyrimidine compound represented by Chemical Formula 1 in a water-miscible solvent such as methanol, ethanol, acetone and 1,4-dioxane, adding a free acid or a free base thereto, and then performing crystallization or recrystallization. Accordingly, the compound of the present invention includes, in addition to the compounds containing various amounts of water that can be prepared through, for example, lyophilization, stoichiometric solvates including hydrates.

Hereunder is given a detailed description about the substituents used to define the compound according to the present invention.

In the present invention, 'halogen atom' means a fluorine, chlorine, bromine or iodine atom.

In the present invention, 'alkyl' means a $C_1$-$C_6$ aliphatic saturated hydrocarbon group, including methyl, ethyl, n-propyl, i-propyl, cyclopropyl, n-butyl, i-butyl, t-butyl, cyclobutyl, cyclopropylmethyl, n-pentyl, i-pentyl, neopentyl, t-pentyl, cyclopentyl, cyclobutylmethyl, n-hexyl, i-hexyl, cyclohexyl, cyclopentylmethyl, etc.

In the present invention, 'haloalkyl' means an alkyl group with one or more hydrogen(s) substituted by halogen atom(s), such as trifluoromethyl.

In the present invention, 'alkoxy' means a hydroxyl group with the hydrogen substituted by a $C_1$-$C_6$ alkyl group substituent, such as methoxy, ethoxy, n-propoxy, i-propoxy, n-butoxy, i-butoxy and t-butoxy.

In the present invention, 'heteroaryl' means a mono-, bi- or tricyclic aromatic heterohydrocarbon group containing one or more heteroatom(s) selected from oxygen, nitrogen and sulfur atoms, such as pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, pyridinyl, pyrazinyl, pyridazinyl, pyrimidinyl, triazolyl, indolyl, isoindolyl, benzofuranyl, benzofurazanyl, dibenzofuranyl, isobenzofuranyl, indazolyl, benzimidazolyl, benzoxazolyl, benzisoxazolyl, benzothiazolyl, dibenzothiophenyl, naphthyridyl, benzisothiazolyl, quinolinyl, isoquinolinyl, quinoxalinyl, phthalazinyl, phthalazinyl, quinazolinyl, or the like.

In the present invention, 'heterocycle' means a heterohydrocarbon ring containing one or more heteroatom(s), such as morpholinyl, piperidinyl, piperazinyl, N-protected piperazinyl, etc.

Preferably, in the 2,7-substituted thieno[3,2-d]pyrimidine compound represented by Chemical Formula 1, A represents heteroaryl selected from thiophenyl, thiazolyl, thiadiazolyl, tetrazolyl, pyridinyl, pyrimidinyl, pyrazinyl, naphthridinyl, benzoimidazolyl, benzothiazolyl, quinazolinyl and dihydroquinazolinyl; $R^a$ represents hydrogen, halogen, oxo (=O), $C_1$-$C_6$ alkyl, $C_1$-$C_6$ alkylcarbonyl, $C_1$-$C_6$ alkoxycarbonyl, amino $C_1$-$C_6$ alkoxy, mono($C_1$-$C_6$ alkyl)amino $C_1$-$C_6$ alkoxy, di($C_1$-$C_6$ alkyl)amino $C_1$-$C_6$ alkoxy, morpholino, piperazinyl, 4-($C_1$-$C_6$ alkyl)piperazinyl, 4-($C_1$-$C_6$ hydroxyalkyl)piperazinyl, or substituted or unsubstituted phenyl; L is nonexistent or represents —NH— or —N($C_1$-$C_6$ alkyl)-; B represents phenyl or quinolinyl; $R^b$ represents hydrogen, $C_1$-$C_6$ haloalkyl, $C_1$-$C_6$ alkoxy, —$(CH_2)_n$—$R^1$, —C(O)$NR^3R^4$, —$NR^2C(O)R^3$, —$NR^2C(O)NR^3R^4$, —$SO_2NR^3R^4$ or —$NR^2SO_2R^3$; n represents an integer from 0 to 3; $R^1$ represents hydrogen, 1,1-dioxidoisothiadiazolidinyl, morpholino, piperidinyl, piperazinyl or 4-($C_1$-$C_6$ alkyl)piperazinyl; $R^2$ represents hydrogen or $C_1$-$C_6$ alkyl; $R^3$ and $R^4$, which are the same or different, represent hydrogen, $C_1$-$C_6$ alkyl, $C_3$-$C_6$ cycloalkyl, $C_1$-$C_6$ haloalkyl, or substituted or unsubstituted phenyl; and the substituted phenyl is substituted with a substituent selected from halogen, $C_1$-$C_6$ haloalkyl, carboxyl and $C_1$-$C_6$ alkoxycarbonyl.

Particularly preferably, in the 2,7-substituted thieno[3,2-d]pyrimidine compound represented by Chemical Formula 1, A represents pyridinyl; $R^a$ represents methyl, ethyl, morpholino, dimethylaminoethoxy, 4-ethylpiperazinyl or 4-(2-hydroxyethyl)piperazinyl; L is nonexistent; B represents phenyl or quinolinyl; and $R^b$ represents hydrogen, —$NHSO_2CH_3$ or —C(O)NH-cyclopropyl.

Specific examples of the 2,7-substituted thieno[3,2-d]pyrimidine compound represented by Chemical Formula 1 include:

N-(3-(2-(6-(4-ethylpiperazin-1-yl)pyridin-3-ylamino)thieno [3,2-d]pyrimidin-7-yl)phenyl)methanesulfonamide;
N-(3-(2-(1H-tetrazol-5-ylamino)thieno[3,2-d]pyrimidin-7-yl)phenyl)methanesulfonamide;
N-(3-(2-(6-fluorobenzo[d]thiazol-2-ylamino)thieno[3,2-d] pyrimidin-7-yl)phenyl)methanesulfonamide;
N-(3-(2-(4,5-dimethylthiazol-2-ylamino)thieno[3,2-d]pyrimidin-7-yl)phenyl)methanesulfonamide;
N-(3-(2-(5-phenyl-1,3,4-thiadiazol-2-ylamino)thieno[3,2-d] pyrimidin-7-yl)phenyl)methanesulfonamide;
N-(3-(2-(4-phenylthiazol-2-ylamino)thieno[3,2-d]pyrimidin-7-yl)phenyl)methanesulfonamide;
N-(3-(2-(pyrazin-2-ylamino)thieno[3,2-d]pyrimidin-7-yl) phenyl)methanesulfonamide;
N-(3-(2-(3H-benzo[d]imidazol-5-ylamino)thieno[3,2-d]pyrimidin-7-yl)phenyl)methanesulfonamide;
N-(3-(2-(5,7-dimethyl-1,8-naphthyridin-2-ylamino)thieno [3,2-d]pyrimidin-7-yl)phenyl)methanesulfonamide;
N-(3-(2-(6-methylbenzo[d]thiazol-2-ylamino)thieno[3,2-d] pyrimidin-7-yl)phenyl)methanesulfonamide;
N-(3-(2-(6-methylpyridin-3-ylamino)thieno[3,2-d]pyrimidin-7-yl)phenyl)methanesulfonamide;
N-(3-(2-(6-morpholinopyridin-3-ylamino)thieno[3,2-d]pyrimidin-7-yl)phenyl)methanesulfonamide;
N-(3-(2-(6-(2-(dimethylamino)ethoxy)pyridin-3-ylamino) thieno[3,2-d]pyrimidin-7-yl)phenyl)methanesulfonamide;
ethyl 3-(5-(7-(3-(methylsulfonamido)phenyl)thieno[3,2-d] pyrimidin-2-ylamino)pyridin-2-yl)benzoate;
ethyl 4-(5-(7-(3-(methylsulfonamido)phenyl)thieno[3,2-d] pyrimidin-2-ylamino)pyridin-2-yl)benzoate;
ethyl 5-(7-(3-(methylsulfonamido)phenyl)thieno[3,2-d]pyrimidin-2-ylamino)nicotinate;
N-(3-(2-(6-morpholinopyrimidin-4-ylamino)thieno[3,2-d] pyrimidin-7-yl)phenyl)methanesulfonamide;
N-(3-(2-(6-(4-ethylpiperazin-1-yl)pyrimidin-4-ylamino) thieno[3,2-d]pyrimidin-7-yl)phenyl)methanesulfonamide;
N-(3-(2-(6-(4-hydroxyethylpiperazin-1-yl)pyridin-3-ylamino)thieno[3,2-d]pyrimidin-7-yl)phenyl)methanesulfonamide;
N-(3-(2-(3-methyl-4-oxo-3,4-dihydroquinazolin-7-ylamino)thieno[3,2-d]pyrimidin-7-yl)phenyl)methanesulfonamide;
N-(3-(2-(5-acetylthiophen-2-ylamino)thieno[3,2-d]pyrimidin-7-yl)phenyl)methanesulfonamide;
7-(4-((4-ethylpiperazin-1-yl)methyl)phenyl)-N-(6-morpholinopyridin-3-yl)thieno[3,2-d]pyridin-2-amine;
N-(6-morpholinopyridin-3-yl)-7-(4-(piperidin-1-ylmethyl) phenyl)thieno[3,2-d]pyrimidin-2-amine;
7-(4-(morpholinomethyl)phenyl)-N-(6-morpholinopyridin-3-yl)thieno[3,2-d]pyrimidin-2-amine;
N-cyclopropyl-3-(2-(6-(4-ethylpiperazin-1-yl)pyridin-3-ylamino)thieno[3,2-d]pyrimidin-7-yl)benzamide;
N-cyclopropyl-3-(2-(6-methylpyridin-3-ylamino)thieno[3, 2-d]pyrimidin-7-yl)benzamide;
N-cyclopropyl-3-(2-(6-morpholinopyridin-3-ylamino) thieno[3,2-d]pyrimidin-7-yl)benzamide;
N-cyclopropyl-3-(2-(6-(4-(2-hydroxyethyl)piperazin-1-yl)-2-methylpyrimidin-4-ylamino)thieno[3,2-d]pyrimidin-7-yl)benzamide;
3-(2-(6-(4-(2-hydroxyethyl)piperazin-1-yl)-2-methylpyrimidin-4-ylamino)thieno[3,2-d]pyrimidin-7-yl)-N-methylbenzenesulfonamide;
N-(6-(4-ethylpiperazin-1-yl)pyridin-3-yl)-7-(quinolin-3-yl) thieno[3,2-d]pyrimidin-2-amine;
N-(6-methylpyridin-3-yl)-7-(quinolin-3-yl)thieno[3,2-d]pyrimidin-2-amine;
N-(6-morpholinopyridin-3-yl)-7-(quinolin-3-yl)thieno[3,2-d]pyrimidin-2-amine;
N-(3-(2-(6-morpholinopyridin-3-ylamino)thieno[3,2-d]pyrimidin-7-yl)phenyl)cyclopropanecarboxamide;
N-(3-(2-(6-morpholinopyridin-3-ylamino)thieno[3,2-d]pyrimidin-7-yl)phenyl)acetamide;
N-(3-(2-(1H-tetrazol-5-ylamino)thieno[3,2-d]pyrimidin-7-yl)phenyl)methanesulfonamide;

N-(3-(2-(6-morpholinopyridin-3-ylamino)thieno[3,2-d]pyrimidin-7-yl)phenyl)isopropylcarboxamide;

4-chloro-N-(3-(2-(6-morpholinopyridin-3-ylamino)thieno[3,2-d]pyrimidin-7-yl)phenyl)-3-(trifluoromethyl)benzamide;

N-(3-(2-(6-morpholinopyridin-3-ylamino)thieno[3,2-d]pyrimidin-7-yl)phenyl)ethanesulfonamide;

N-(3-(2-(6-morpholinopyridin-3-ylamino)thieno[3,2-d]pyrimidin-7-yl)phenyl)cyclopropanesulfonamide;

1-(4-chloro-3-(trifluoromethyl)phenyl)-3-(3-(2-(6-morpholinopyridin-3-ylamino)thieno[3,2-d]pyrimidin-7-yl)phenyl)urea;

1-cyclohexyl-3-(3-(2-(6-morpholinopyridin-3-ylamino)thieno[3,2-d]pyrimidin-7-yl)phenyl)urea;

1-(3-(2-(6-morpholinopyridin-3-ylamino)thieno[3,2-d]pyrimidin-7-yl)phenyl)-3-(2,2,2-trifluoroethyl)urea;

N-(6-(4-ethylpiperazin-1-yl)pyridin-3-yl)-7-(2-(trifluoromethyl)phenyl)thieno[3,2-d]pyrimidin-2-amine;

N-(6-morpholinopyridin-3-yl)-7-(2-(trifluoromethyl)phenyl)thieno[3,2-d]pyrimidin-2-amine;

N-(3-(2-(6-(4-ethylpiperazin-1-yl)pyridin-3-ylamino)thieno[3,2-d]pyrimidin-7-yl)phenyl)-N-methylmethanesulfonamide;

N-methyl-N-(3-(2-(6-methylpyridin-3-ylamino)thieno[3,2-d]pyrimidin-7-yl)phenyl)methanesulfonamide;

N-methyl-N-(3-(2-(6-morpholinopyridin-3-ylamino)thieno[3,2-d]pyrimidin-7-yl)phenyl)methanesulfonamide;

$N^2$-(6-morpholinopyridin-3-yl)-$N^7$-(3,4,5-trimethoxyphenyl)thieno[3,2-d]pyrimidin-2,7-diamine;

$N^7$-methyl-$N^2$-(6-morpholinopyridin-3-yl)-$N^7$-(3,4,5-trimethoxyphenyl)thieno[3,2-d]pyrimidin-2,7-diamine;

7-(3-(1,1-dioxido-2-isothiadiazolidinyl)phenyl)-N-(6-(4-ethylpiperazin-1-yl)pyridin-3-yl)thieno[3,2-d]pyrimidin-2-amine; and N-(3-(2-(6-(4-ethylpiperazin-1-yl)pyridin-3-ylamino)thieno[3,2-d]pyrimidin-7-yl)phenyl)methanesulfonamide hydrochloride.

The present invention also provides a method for preparing the 2,7-substituted thieno[3,2-d]pyrimidine compound represented by Chemical Formula 1. A typical example is Scheme 1.

According to Scheme 1, the 2,7-substituted thieno[3,2-d]pyrimidine compound represented by Chemical Formula 1 is prepared by two coupling reactions:

[Scheme 1]

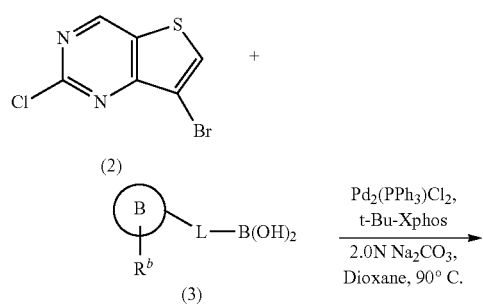

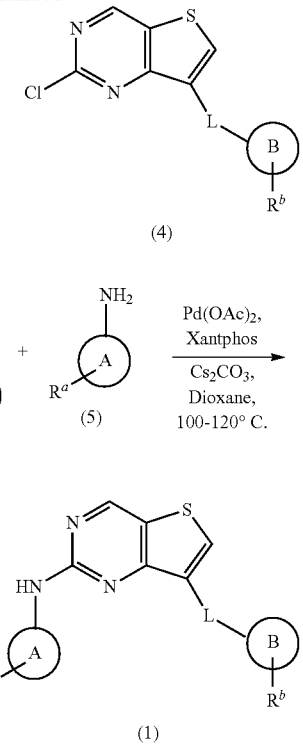

wherein A, B, $R^a$ and $R^b$ are the same as defined above.

In the first coupling reaction, the 7-bromo-2-chlorothieno[3,2-d]pyrimidine represented by Chemical Formula 2 is subjected to Suzuki coupling reaction with the boronic acid compound or Buchwald amination reaction represented by Chemical Formula 3 to prepare the compound represented by Chemical Formula 4 with the group B introduced at the C-7 position.

In the second coupling reaction, the compound represented by Chemical Formula 4 is subjected to Buchwald amination reaction with the amine compound represented by Chemical Formula 5 to prepare the 2,7-substituted thieno[3,2-d]pyrimidine compound represented by Chemical Formula 1.

In the Suzuki coupling reaction and the Buchwald amination reaction of Scheme 1, $Pd_2(dba)_3$, $Pd(OAc)_2$, $PdCl_2(PPh_3)_2$, $Pd(PPh_3)_4$, etc. may be used as a metal catalyst. And, Xantphos (CAS number: 161265-03-8), Davephos (CAS number: 213697-53-1), Johnphos (CAS number: 224311-51-7), X-phos (CAS number: 564483-18-7), tert-butyl Xphos (CAS number: 564483-19-8), etc., may be used as a ligand. And, carbonate, sulfate, phosphate, alkoxide, etc. of an alkali metal or alkaline earth metal may be used as a base. Specific examples include $K_2CO_3$, $CsCO_3$, $Na_2CO_3$, $K_3PO_4$, NaOt-Bu, KOt-Bu, etc.

In the coupling reaction, a commonly used organic solvent including tetrahydrofuran, dioxane, N,N-dimethylformamide, N,N-dimethylsulfoxide, 2-butanol, 2-pentanol, or the like may be used as a reaction solvent. The reaction temperature is maintained at 50 to 200° C., preferably at 80 to 150° C.

The 7-bromo-2-chlorothieno[3,2-d]pyrimidin-4-amine compound represented by Chemical Formula 2, which is used as a starting material in Scheme 1, may be prepared according to Scheme 2:

[Scheme 2]

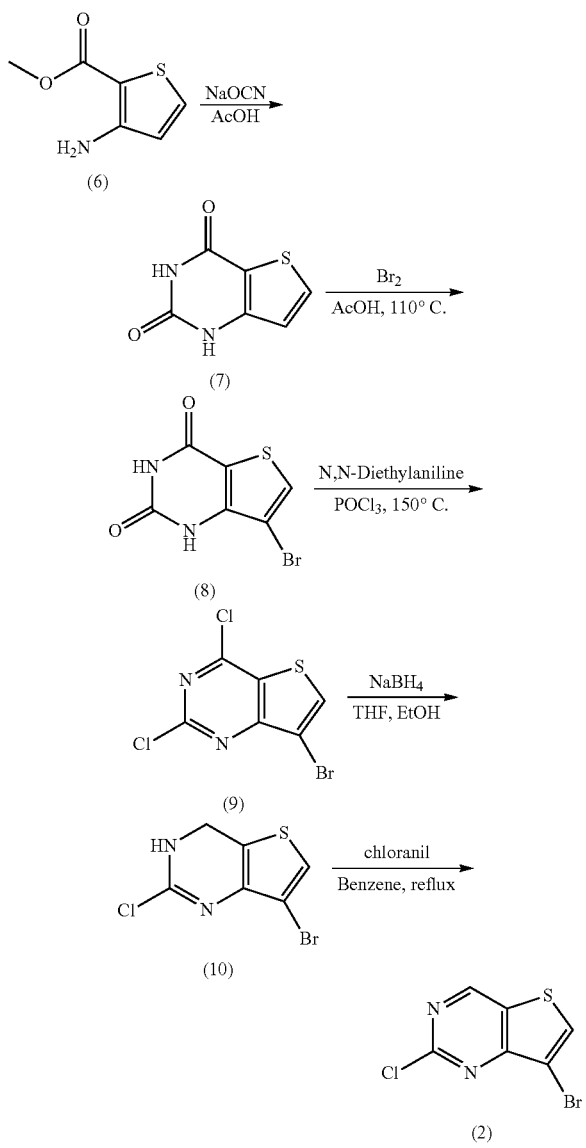

According to Scheme 2, the 7-bromo-2-chlorothieno[3,2-d]pyrimidin-4-amine compound represented by Chemical Formula 2 is prepared through the following 5-step process.

In the first step, a pyrimidin-2,4-dione backbone is formed through cyclization of the amino group and the ester group of the methyl 3-aminothiophen-2-carboxylate compound represented by Chemical Formula 6, using sodium cyanate (NaOCN).

In the second step, a bromo group is introduced at the C-7 position of the thieno[3,2-d]pyrimidin-2,4(1H,3H)-dione compound represented by Chemical Formula 7. This step may be performed at high temperature (110° C.) using bromine in the presence of acetic acid.

In the third step, the pyrimidin-2,4(1H,3H)-dione ring of the 7-bromothieno[3,2-d]pyrimidin-2,4(1H,3H)-dione compound represented by Chemical Formula 8 is converted into a 2,4-dichloropyrimidine ring. This step may be performed at high temperature (150° C.) using phosphorus oxychloride (POCl₃) in the presence of N,N-dimethylaniline.

In the fourth step, the chloro group at the C-4 position of the 7-bromo-2,4-dichlorothieno[3,2-d]pyrimidine represented by Chemical Formula 9 is removed and the N3-C4 bond is reduced. This step may be performed using sodium borohydride (NaBH₄) in an ethanol/tetrahydrofuran (THF) solvent.

Finally, in the fifth step, the N3-C4 bond of the 7-bromo-2-chloro-3,4-dihydrothieno[3,2-d]pyrimidine compound represented by Chemical Formula 10 is oxidized. This step may be performed through stirring under reflux in a benzene solvent using chloranil (2,3,5,6-tetrachloro-p-benzoquinone) as an oxidizing agent.

The 2,7-substituted thieno[3,2-d]pyrimidine compound represented by Chemical Formula 1, an isomer thereof, a pharmaceutically acceptable salt thereof, a solvate thereof and a hydrate thereof may be used as an agent for preventing or treating diseases caused by abnormal cell growth because they exhibit superior inhibition activity against various protein kinases, e.g., KDR, ALK, Aurora A, Kit, Src, EphA1, Flt3, Fms, Itk, Met, Ret, Syk, Tie2 and TrkB. Examples of the diseases caused by abnormal cell growth include various tumors such as stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma, fibroadenoma, or the like.

Accordingly, the present invention provides a pharmaceutical composition comprising the 2,7-substituted thieno[3,2-d]pyrimidine compound represented by Chemical Formula 1, a pharmaceutically acceptable salt thereof, a solvate thereof or a hydrate thereof as an effective ingredient, and an agent for preventing and treating various tumors caused by abnormal cell growth.

The pharmaceutical composition of the present invention comprises the 2,7-substituted thieno[3,2-d]pyrimidine compound represented by Chemical Formula 1, a pharmaceutically acceptable salt thereof, a solvate thereof or a hydrate thereof as an effective ingredient and may further include a commonly used, nontoxic, pharmaceutically acceptable carrier, adjuvant, excipient, or the like to prepare formulations commonly used in the pharmaceutical field, for example, formulations for oral administration such as tablet, capsule, troche, liquid, suspension, etc., and formulations for parenteral administration.

The excipient that may be used in the pharmaceutical composition of the present invention includes sweetener, binder, solubilizer, wetting agent, emulsifier, isotonic agent, adsorbent, disintegrant, antioxidant, preservative, lubricant, filler, aromatic, or the like. For example, lactose, dextrose, sucrose, mannitol, sorbitol, cellulose, glycine, silica, talc, stearic acid, stearin, magnesium stearate, magnesium aluminum silicate, starch, gelatin, gum tragacanth, alginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor, etc., may be used.

The administration dose of the compound according to the present invention may vary depending on the patient's age, body weight, sex and physical conditions, administration type, severity of disease, or the like. Based on an adult patient weighing 70 kg, the administration dose may be in general 0.01 to 1,000 mg/day. As per the decision by a physician or a pharmacist, the administration may be once to several times a day with predetermined time intervals.

Mode for Invention

The examples, formulation examples and test examples will now be described. However, the following examples, formulation examples and test examples are for illustrative purposes only and not intended to limit the scope of the present invention.

EXAMPLES

Example 1

N-(3-(2-(6-(4-ethylpiperazin-1-yl)pyridin-3-ylamino)thieno[3,2-d]pyrimidin-7-yl)phenyl)methanesulfonamide The compound of Example 1 represented by the following structural formula was prepared by a 10-step synthesis process as follows.

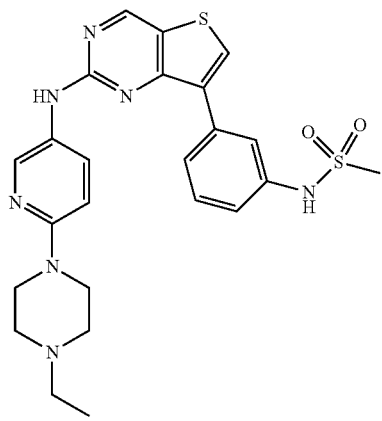 [SMILES: CCN1CCN(c2ccc(Nc3ncc4scc(-c5cccc(NS(C)(=O)=O)c5)c4n3)cn2)CC1]

Step 1: thieno[3,2-d]pyridin-2,4(1H,3H)-dione

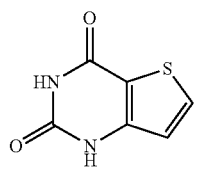 [SMILES: O=c1[nH]c(=O)c2sccc2[nH]1]

To a solution in which sodium cyanate (5.0 g, 77.0 mmol) was dissolved in water (15.0 mL), methyl 3-aminothiophen-2-carboxylate (6.05 g, 38.4 mmol) dissolved in a mixture solution (90 mL) of 50% glacial acetic acid and water was slowly added dropwise. After stirring for 5 hours at room temperature, thus prepared white precipitate was filtered. The white solid was dissolved in 2.0 N sodium hydroxide solution (90.0 mL). The mixture solution was cooled to 0° C. and acidified using acetic acid. Filtration of thus prepared white solid followed by drying yielded the target compound thieno[3,2-d]pyrimidin-2,4(1H,3H)-dione (5.2 g, 81% yield).

$^1$H NMR (400 MHz, DMSO-$d_6$) δ 11.33 (bs, 2H), 8.10 (d, J=5.2 Hz, 1H), 8.10 (d, J=5.2 Hz, 1H), MS m/z: 168.94 [M+1].

Step 2:
7-bromothieno[3,2-d]pyrimidin-2,4(1H,3H)-dione

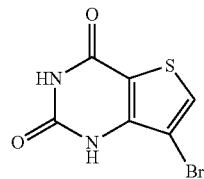 [SMILES: O=c1[nH]c(=O)c2scc(Br)c2[nH]1]

To a solution in which thieno[3,2-d]pyrimidin-2,4(1H,3H)-dione (5.0 g, 29.5 mmol) was dissolved in glacial acetic acid (200 mL), bromine (4.55 mL, 89.0 mmol) was added. The reaction mixture solution was stirred at 110° C. for 30 hours, cooled to room temperature, and then slowly added to ice water (400 mL). Drying of thus prepared solid followed by filtration, washing several times with water and drying yielded the target compound 7-bromothieno[3,2-d]pyrimidin-2,4(1H,3H)-dione (6.5 g, 90% yield).

$^1$H NMR (400 MHz, DMSO-$d_6$) δ 11.54 (s, 1H), 11.42 (s, 1H), 8.24 (s, 1H), MS m/z: 247.34, 249.32 [M+1].

Step 3:
7-bromo-2,4-dichlorothieno[3,2-d]pyrimidine

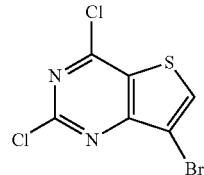

Phosphoryl chloride (24.6 mL, 267 mmol) was added to 7-bromothieno[3,2-d]pyrimidin-2,4(1H,3H)-dione (6.6 g, 26.7 mmol), and then N,N-diethylaniline (17.1 mL, 106.8 mmol) was slowly added thereto. The reaction mixture solution was stirred at 150° C. for 5 hours. The mixture solution was cooled to room temperature and then slowly added to ice water (300 mL). Washing of thus prepared solid with ice water followed by drying yielded the target compound 7-bromo-2,4-dichlorothieno[3,2-d]pyrimidine (6.2 g, 82% yield).

$^1$H NMR (400 MHz, DMSO-$d_6$) δ 8.40 (s, 1H), MS m/z: 282.96, 284.96, 286.96 [M+1].

Step 4: 7-bromo-2-chloro-3,4-dihydrothieno[3,2-d]pyrimidine

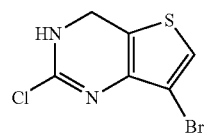 [SMILES: ClC1=Nc2c(Br)csc2CN1]

7-Bromo-2,4-dichlorothieno[3,2-d]pyrimidine (1000 mg, 3.54 mmol) was dissolved in tetrahydrofuran-ethanol (1/1, 30 mL) and sodium borohydride (670 mg, 17.74 mmol) was added in several aliquots. The reaction mixture solution was cooled to room temperature and stirred for an hour. After adding water to terminate the reaction, the mixture solution was extracted with dichloromethane. The organic layer was washed with brine, dried with magnesium sulfate, and then concentrated. The yielded 7-bromo-2-chloro-3,4-dihydrothieno[3,2-d]pyrimidine (720 mg, 81% yield) was used without purification.

$^1$H NMR (400 MHz, DMSO-d$_6$) δ 8.38 (s, 1H), 7.49 (s, 1H), 4.78 (s, 2H), MS m/z: 252.87, 252.89 [M+1].

Step 5: 7-bromo-2-chlorothieno[3,2-d]pyrimidine

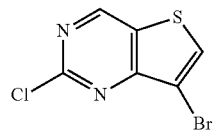 [SMILES: Clc1ncc2scc(Br)c2n1]

7-Bromo-2-chloro-3,4-dihydrothieno[3,2-d]pyrimidine (750 mg, 3.0 mmol) and chloranil (740 mg, 3.0 mmol) were dissolved in benzene (30 mL) and stirred for 3 hours under reflux. The reaction mixture was cooled to room temperature and diluted with benzene (30 mL). The mixture solution was washed with 0.5 N sodium hydroxide (30 mL) solution and water. The organic layer was dried with magnesium sulfate and then concentrated. Purification of the resultant compound by chromatography (10% ethyl acetate/hexane) yielded the target compound (630 mg, 85% yield) as white solid.

$^1$H NMR (400 MHz, DMSO-d$_6$) δ 9.55 (s, 1H), 8.81 (s, 1H), MS m/z: 248.87, 250.87 [M+1].

Step 6: 3-(2-chlorothieno[3,2-d]pyrimidin-7-yl)benzenamine

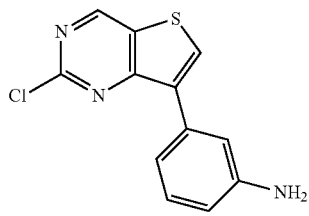 [SMILES: Nc1cccc(-c2csc3cnc(Cl)nc23)c1]

7-Bromo-2-chlorothieno[3,2-d]pyrimidine (3.645 g, 14.61 mmol) was dissolved in dioxane (44 mL) and 2.0 N sodium carbonate (22 mL, 43.83 mmol) and 3-aminophenylboronic acid (2 g, 14.61 mmol) were added. After flowing nitrogen to the mixture solution for 10 minutes, Pd$_2$(PPh$_3$)Cl$_2$ (615 mg, 0.88 mmol) and t-ButylXphos (558 mg, mmol) were added. The reaction mixture solution was stirred at 90° C. for 6 hours and filtered with celite. The filtrate was diluted with ethyl acetate and washed with brine. The organic layer was concentrated by drying with magnesium sulfate. Purification by chromatography (20% ethyl acetate/hexane) yielded the target compound (2.8 g, 73% yield).

$^1$H NMR (400 MHz, CDCl$_3$) δ 9.14 (s, 1H), 8.10 (s, 1H), 7.31 (s, 1H), 7.27 (d, J=6.4 Hz, 2H), 6.74 (m, 1H), 3.85 (br, 2H), MS m/z: 262.04, 264.03 [M+1].

Step 7: N-(3-(2-chlorothieno[3,2-d]pyrimidin-7-yl)phenyl)methanesulfonamide

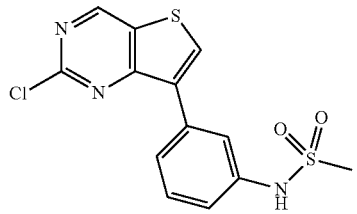 [SMILES: CS(=O)(=O)Nc1cccc(-c2csc3cnc(Cl)nc23)c1]

3-(2-Chlorothieno[3,2-d]pyrimidin-7-yl)benzenamine (800 mg, 3.06 mmol) was dissolved in anhydrous tetrahydrofuran (15 mL) and methanesulfonyl chloride (0.27 mL, 3.37 mmol) and triethylamine (0.85 mL, 6.13 mmol) were added. The mixture solution was stirred for 2 hours, diluted with ethyl acetate, and then washed with brine. The organic layer was concentrated by drying with magnesium sulfate. Purification by chromatography (10% ethyl acetate/hexane) yielded the target compound (950 mg, 91% yield).

$^1$H NMR (400 MHz, CDCl$_3$) δ 9.19 (s, 1H), 8.23 (s, 1H), 7.94 (t, 1H), 7.71 (dt, 1H), 7.49 (t, 1H), 7.22 (m, 1H), 6.64 (s, 1H), 3.17 (s, 3H), MS m/z: 340.02, 342.00 [M+1].

Step 8: 1-ethyl-4-(5-nitro pyridin-2-yl)piperazine

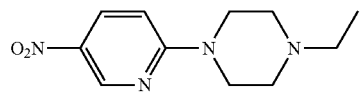

2-Chloro-5-nitropyridine (800 mg, 5.05 mmol) was dissolved in dioxane (20 mL) and then 1-ethylpiperazine (1.7 g, 15.15 mmol) and N,N-diisopropylethylamine (927 mL, 5.05 mmol) were added. The reaction mixture solution was stirred at 70° C. for a day. The reaction solution was cooled to room temperature, diluted with ethyl acetate, and then washed with brine. The organic layer was concentrated by drying with magnesium sulfate. The target compound (1.05 g, 87% yield) was used in the following reaction without purification.

MS m/z: 237.51 [M+1].

Step 9: 6-(4-ethylpiperazin-1-yl)pyridin-3-amine

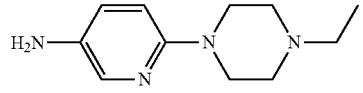

1-Ethyl-4-(5-nitropyridin-2-yl)piperazine (3.09 g, 13.8 mmol) was dissolved in methanol (69 mL) and 10% Pd/C (300 mg) was added. The reaction mixture was stirred at room temperature for a day under a pressure of a balloon filled with hydrogen gas. The reaction mixture solution was concentrated by filtering with celite. The resultant target compound (2.4 g, 89% yield) was used in the following reaction without purification.

$^1$H NMR (400 MHz, DMSO-d$_6$) δ 7.59 (d, J=2.8 Hz, 1H), 6.89 (dd, J=2.8 Hz, J=8.8 Hz, 1H), 6.63 (d, J=7.2 Hz, 1H), 4.54 (s, 2H), 3.18 (m, 4H), 2.42 (m, 4H), 2.32 (q, 2H), 1.01 (t, 3H), MS m/z: 207.44 [M+1].

Step 10: N-(3-(2-(6-(4-ethylpiperazin-1-yl)pyridin-3-ylamino)thieno[3,2-d]pyrimidin-7-yl)phenyl)methanesulfonamide

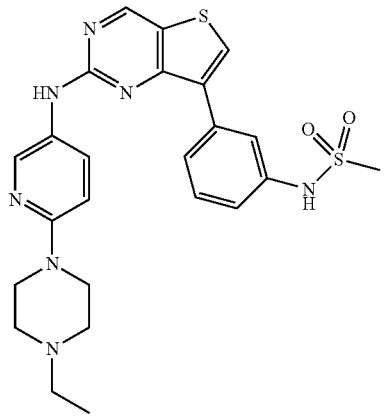 [SMILES: CCN1CCN(c2ccc(Nc3ncc4scc(-c5cccc(NS(C)(=O)=O)c5)c4n3)cn2)CC1]

N-(3-(2-chlorothieno[3,2-d]pyrimidin-7-yl)phenyl)methanesulfonamide (20 mg, 0.059 mmol) was dissolved in dioxane (1 mL) and then cesium carbonate (58 mg, 0.18 mmol) and 6-(4-ethylpiperazin-1-yl)pyridin-3-amine (18 mg, 0.088 mmol) were added. After flowing nitrogen gas to the reaction mixture for 10 minutes, Pd(OAc)$_2$ (1 mg, 0.1 mmol) and Xantphos (4 mg, 0.12 mmol) were added. The reaction mixture was stirred at 120° C. for 6 hours and filtered with celite. The filtrate was diluted with ethyl acetate and washed with brine. The organic layer was dried with magnesium sulfate and concentrated by filtering with celite. Purification by chromatography (5% methanol/dichloromethane) yielded the target compound (16 mg, 53% yield).

$^1$H NMR (400 MHz, DMSO-d$_6$) δ 9.82 (s, 1H), 9.58 (s, 1H), 9.23 (s, 1H), 8.55 (m, 1H), 8.48 (s, 1H), 8.17 (dd, J=2.4 Hz, J=8.9 Hz, 1H), 7.78 (s, 1H), 7.76 (d, J=7.8 Hz, 1H), 7.46 (t, 1H), 7.29 (dd, J=1.1 Hz, J=8.4 Hz, 1H), 7.00 (d, J=9.2 Hz, 1H), 4.33 (m, 2H), 3.21 (m, 2H), 3.10 (m, 6H), 3.05 (s, 3H), 1.25 (t, 3H), MS m/z: 510.60 [M+1].

Examples 2 to 18

The target compounds of Examples 2 to 18 were prepared through Buchwald amination reaction of the N-(3-(2-chlorothieno[3,2-d]pyrimidin-7-yl)phenyl)methanesulfonamide synthesized in Step 7 of Example 1 with various amine compounds, according to the following reaction scheme. The condition of the Buchwald amination reaction was the same as that of Step 10 of Example 1.

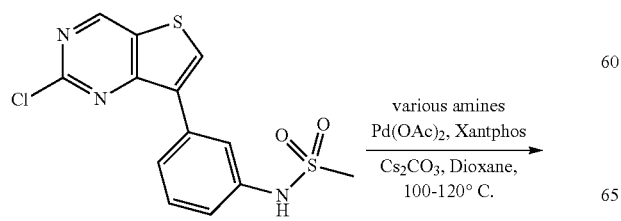

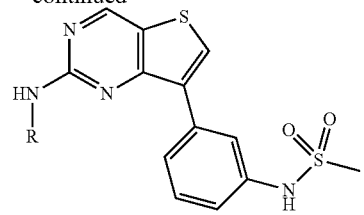

Example 2

N-(3-(2-(1H-tetrazol-5-ylamino)thieno[3,2-d]pyrimidin-7-yl)phenyl)methanesulfonamide

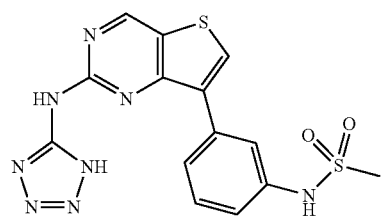 [SMILES: CS(=O)(=O)Nc1cccc(-c2csc3cnc(Nc4nnn[nH]4)nc23)c1]

MS m/z: 389.48 [M+1].

Example 3

N-(3-(2-(6-fluorobenzo[d]thiazol-2-ylamino)thieno[3,2-d]pyrimidin-7-yl)phenyl)methanesulfonamide

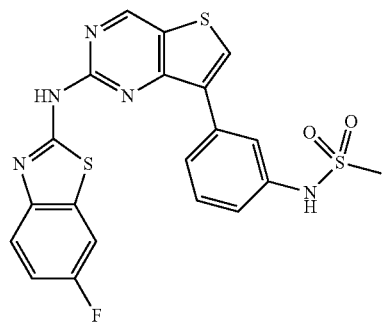 [SMILES: CS(=O)(=O)Nc1cccc(-c2csc3cnc(Nc4nc5ccc(F)cc5s4)nc23)c1]

MS m/z: 472.54 [M+1].

Example 4

N-(3-(2-(4,5-dimethylthiazol-2-ylamino)thieno[3,2-d]pyrimidin-7-yl)phenyl)methanesulfonamide

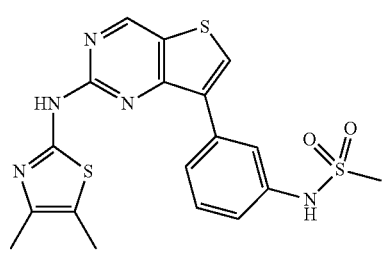

MS m/z: 432.45 [M+1].

Example 5

N-(3-(2-(5-phenyl-1,3,4-thiadiazol-2-ylamino)thieno[3,2-d]pyrimidin-7-yl)phenyl)methanesulfonamide

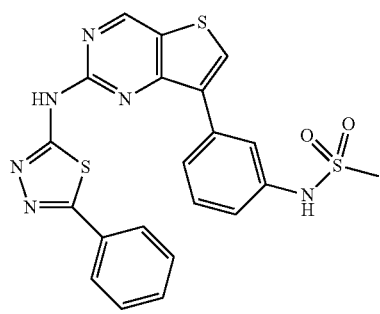 [SMILES: CS(=O)(=O)Nc1cccc(-c2csc3cnc(Nc4nnc(-c5ccccc5)s4)nc23)c1]

MS m/z: 481.54 [M+1].

Example 6

N-(3-(2-(4-phenylthiazol-2-ylamino)thieno[3,2-d]pyrimidin-7-yl)phenyl)methanesulfonamide

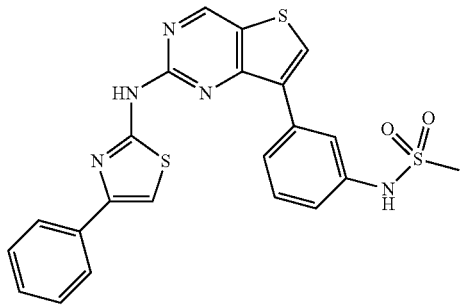 [SMILES: CS(=O)(=O)Nc1cccc(-c2csc3cnc(Nc4nc(-c5ccccc5)cs4)nc23)c1]

MS m/z: 480.46 [M+1].

Example 7

N-(3-(2-(pyrazin-2-ylamino)thieno[3,2-d]pyrimidin-7-yl)phenyl)methanesulfonamide

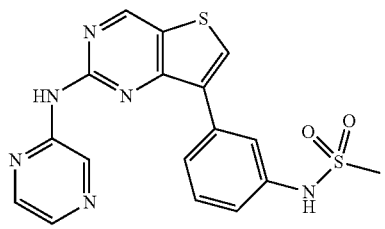 [SMILES: CS(=O)(=O)Nc1cccc(-c2csc3cnc(Nc4cnccn4)nc23)c1]

MS m/z: 399.58 [M+1].

Example 8

N-(3-(2-(3H-benzo[d]imidazol-5-ylamino)thieno[3,2-d]pyrimidin-7-yl)phenyl)methanesulfonamide

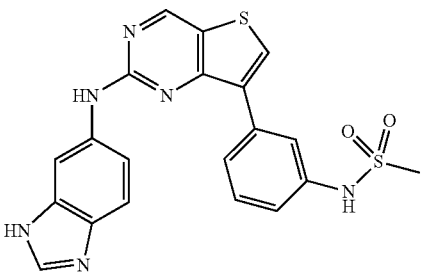 [SMILES: CS(=O)(=O)Nc1cccc(-c2csc3cnc(Nc4ccc5nc[nH]c5c4)nc23)c1]

MS m/z: 437.61 [M+1].

Example 9

N-(3-(2-(5,7-dimethyl-1,8-naphthyridin-2-ylamino)thieno[3,2-d]pyrimidin-7-yl)phenyl)methanesulfonamide

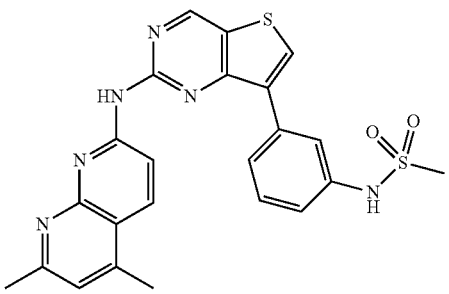

MS m/z: 477.65 [M+1].

Example 10

N-(3-(2-(6-methylbenzo[d]thiazol-2-ylamino)thieno[3,2-d]pyrimidin-7-yl)phenyl)methanesulfonamide

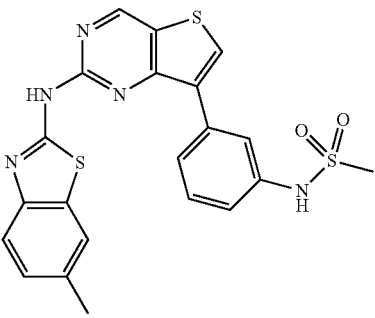 [SMILES: Cc1ccc2nc(Nc3ncc4scc(-c5cccc(NS(C)(=O)=O)c5)c4n3)sc2c1]

$^1$H NMR (DMSO-d$_6$) δ 9.89 (s, 1H), 9.43 (s, 1H), 8.63 (s, 1H), 7.90 (s, 1H), 7.84 (d, J=7.5 Hz, 1H), 7.73 (s, 1H), 7.56

(m, 3H), 7.36 (d, J=8.1 Hz, 1H), 7.22 (d, J=8.1 Hz, 1H), 3.06 (s, 3H), 2.44 (s, 3H), MS m/z: 468.72 [M+1].

Example 11

N-(3-(2-(6-methylpyridin-3-ylamino)thieno[3,2-d]pyrimidin-7-yl)phenyl)methanesulfonamide

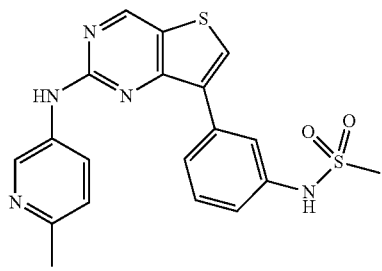 [SMILES: Cc1ccc(Nc2ncc3scc(-c4cccc(NS(C)(=O)=O)c4)c3n2)cn1]

¹H NMR (DMSO-d₆) δ 10.16 (s, 1H), 9.86 (s, 1H), 9.32 (s, 1H), 9.03 (d, J=2.0 Hz, 1H), 8.54 (s, 1H), 8.39 (dd, J=2.1 Hz, J=8.6 Hz, 1H), 7.74 (m, 2H), 7.50 (m, 2H), 7.30 (d, J=8.0 Hz, 1H), 3.05 (s, 3H), 2.54 (s, 3H), MS m/z: 412.46 [M+1].

Example 12

N-(3-(2-(6-morpholinopyridin-3-ylamino)thieno[3,2-d]pyrimidin-7-yl)phenyl)methanesulfonamide

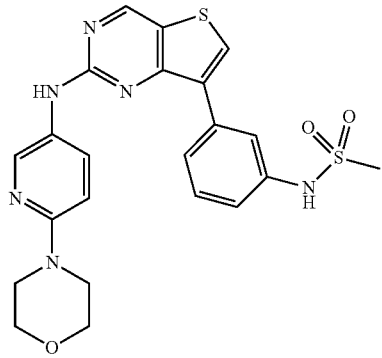 [SMILES: CS(=O)(=O)Nc1cccc(-c2csc3cnc(Nc4ccc(N5CCOCC5)nc4)nc23)c1]

¹H NMR (DMSO-d₆) δ 9.83 (s, 1H), 9.67 (s, 1H), 9.23 (s, 1H), 8.50 (s, 1H), 8.49 (d, J=2.5 Hz, 1H), 8.24 (d, J=9.2 Hz, 1H), 7.78 (s, 1H), 7.62 (d, J=7.8 Hz, 1H), 7.47 (t, 1H), 7.26 (m, 1H), 7.08 (m, 1H), 3.74 (m, 4H), 3.45 (m, 4H), 3.03 (s, 3H), MS m/z: 483.53 [M+1].

Example 13

N-(3-(2-(6-(2-(dimethylamino)ethoxy)pyridin-3-ylamino)thieno[3,2-d]pyrimidin-7-yl)phenyl)methanesulfonamide

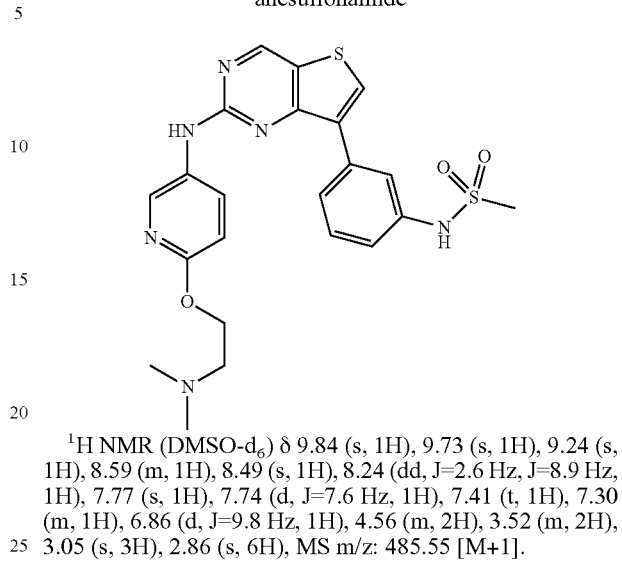

¹H NMR (DMSO-d₆) δ 9.84 (s, 1H), 9.73 (s, 1H), 9.24 (s, 1H), 8.59 (m, 1H), 8.49 (s, 1H), 8.24 (dd, J=2.6 Hz, J=8.9 Hz, 1H), 7.77 (s, 1H), 7.74 (d, J=7.6 Hz, 1H), 7.41 (t, 1H), 7.30 (m, 1H), 6.86 (d, J=9.8 Hz, 1H), 4.56 (m, 2H), 3.52 (m, 2H), 3.05 (s, 3H), 2.86 (s, 6H), MS m/z: 485.55 [M+1].

Example 14

Ethyl 3-(5-(7-(3-(methylsulfonamido)phenyl)thieno[3,2-d]pyrimidin-2-ylamino)pyridin-2-yl)benzoate

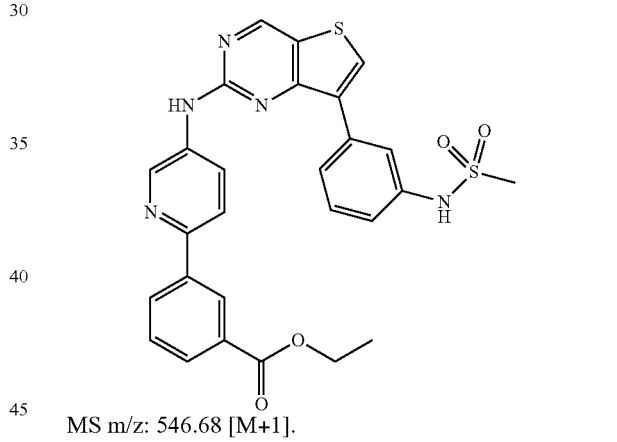

MS m/z: 546.68 [M+1].

Example 15

Ethyl 4-(5-(7-(3-(methylsulfonamido)phenyl)thieno[3,2-d]pyrimidin-2-ylamino)pyridin-2-yl)benzoate

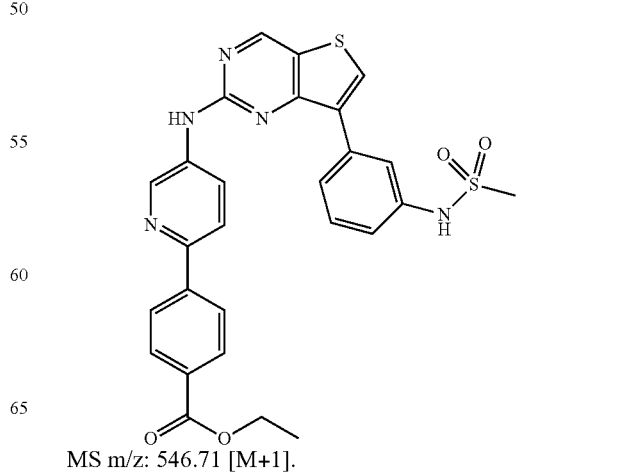

MS m/z: 546.71 [M+1].

Example 16

Ethyl 5-(7-(3-(methylsulfonamido)phenyl)thieno[3,2-d]pyrimidin-2-ylamino)nicotinate

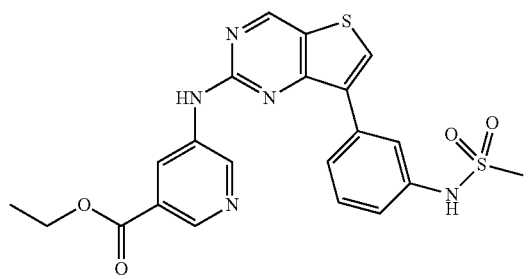 [SMILES: CCOC(=O)c1cncc(Nc2ncc3scc(-c4cccc(NS(C)(=O)=O)c4)c3n2)c1]

MS m/z: 470.71 [M+1].

Example 17

N-(3-(2-(6-morpholinopyrimidin-4-ylamino)thieno[3,2-d]pyrimidin-7-yl)phenyl)methanesulfonamide

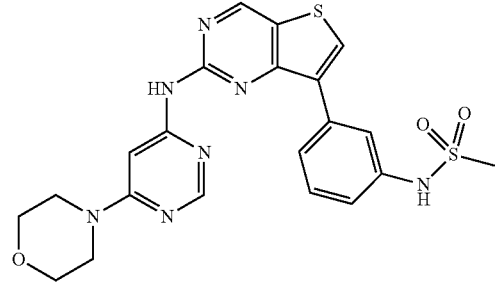 [SMILES: CS(=O)(=O)Nc1cccc(-c2csc3cnc(Nc4cc(N5CCOCC5)ncn4)nc23)c1]

MS m/z: 484.04 [M+1].

Example 18

N-(3-(2-(6-(4-ethylpiperazin-1-yl)pyrimidin-4-ylamino)thieno[3,2-d]pyridin-7-yl)phenyl)methanesulfonamide

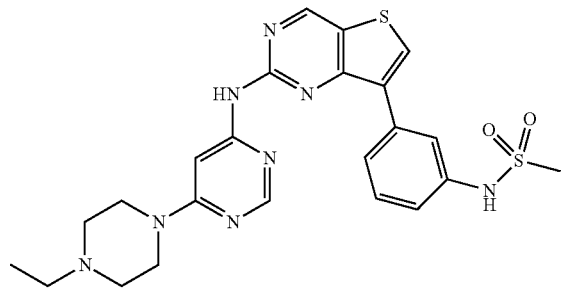 [SMILES: CCN1CCN(c2cc(Nc3ncc4scc(-c5cccc(NS(C)(=O)=O)c5)c4n3)ncn2)CC1]

MS m/z: 511.07 [M+1].

Example 19

N-(3-(2-(6-(4-hydroxyethylpiperazin-1-yl)pyridin-3-ylamino)thieno[3,2-d]pyrimidin-7-yl)phenyl)methanesulfonamide The compound of Example 19 represented by the following structural formula was prepared by a 4-step synthesis process as follows.

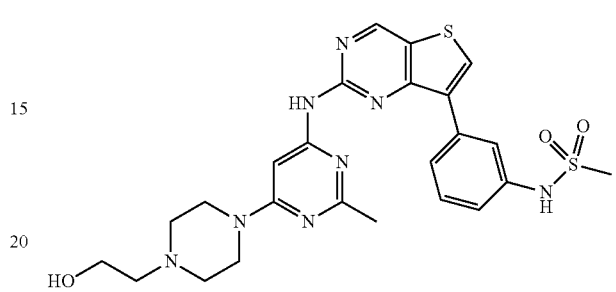

Step 1: 7-bromothieno[3,2-d]pyrimidin-2-amine

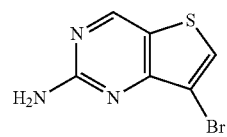

7-Bromo-2-chlorothieno[3,2-d]pyrimidine (1.0 g, 4.03 mmol) was dissolved in 2.0 M ammonia isopropanol (10 mL) and stirred at 100° C. for 48 hours in a sealed reactor. The reaction mixture was cooled to room temperature and then concentrated. Purification by chromatography (50% ethyl acetate/hexane) yielded a brown solid compound (560 mg, 60% yield).

$^1$H NMR (400 MHz, DMSO-$d_6$) δ 8.95 (s, 1H), 8.36 (s, 1H), 6.89 (s, 2H), MS m/z: 230.26, 232.26 [M+1].

Step 2: 7-(3-aminophenyl)thieno[3,2-d]pyrimidin-2-amine

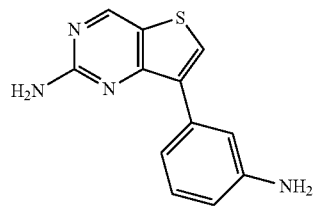 [SMILES: Nc1cccc(-c2csc3cnc(N)nc23)c1]

7-(3-Aminophenyl)thieno[3,2-d]pyrimidin-2-amine (160 mg, 75% yield) was prepared in the same manner as Step 6 of Example 1 using 7-bromothieno[3,2-d]pyrimidin-2-amine (200 mg, 0.87 mmol) and 3-aminophenylboronic acid (120 mg, 0.87 mmol).

$^1$H NMR (400 MHz, DMSO-$d_6$) δ 8.96 (s, 1H), 8.20 (s, 1H), 7.64 (m, 2H), 7.07 (m, 2H), 6.56 (s, 2H), 5.04 (s, 2H), MS m/z: 243.30 [M+1].

Step 3: N-(3-(2-aminothieno[3,2-d]pyrimidin-7-yl) phenyl)methanesulfonamide

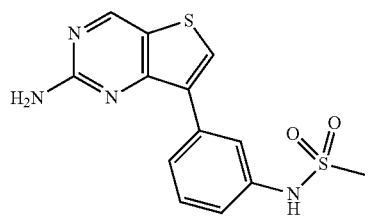 [SMILES: CS(=O)(=O)Nc1cccc(-c2csc3cnc(N)nc23)c1]

N-(3-(2-Aminothieno[3,2-d]pyrimidin-7-yl)phenyl)methanesulfonylamide (182 mg, 86% yield) was prepared in the same manner as Step 7 of Example 1 using 7-(3-aminophenyl)thieno[3,2-d]pyrimidin-2-amine (160 mg, 0.66 mmol).

$^1$H NMR (400 MHz, DMSO-$d_6$) δ 9.00 (s, 1H), 8.36 (s, 1H), 7.78 (s, 1H), 7.74 (d, 1H), 7.71 (m, 1H), 7.40 (t, 1H), 7.15 (m, 1H), 6.56 (s, 2H), 3.05 (s, 3H), MS m/z: 320.99 [M+1].

Step 4: N-(3-(2-(6-(4-(2-hydroxyethyl)piperazin-1-yl)-2-methylpyrimidin-4-ylamino)thieno[3,2-d]pyrimidin-7-yl)phenyl)methanesulfonamide

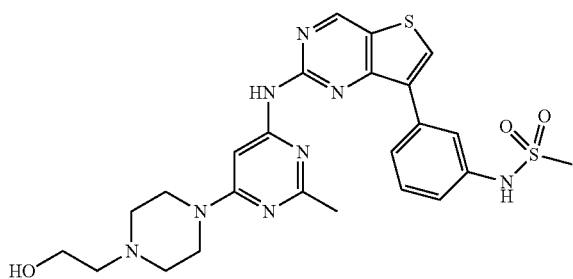 [SMILES: Cc1nc(Nc2ncc3scc(-c4cccc(NS(C)(=O)=O)c4)c3n2)cc(N2CCN(CCO)CC2)n1]

N-(3-(2-(6-(4-(2-Hydroxyethyl)piperazin-1-yl)-2-methylpyrimidin-4-ylamino)thieno[3,2-d]pyrimidin-7-yl)phenyl) methanesulfonamide (18 mg, 53% yield) was prepared in the same manner as Step 10 of Example 1 using N-(3-(2-aminothieno[3,2-d]pyrimidin-7-yl)phenyl)methanesulfonamide (20 mg, 0.062 mmol) and 2-(4-(6-chloro-2-methylpyrimidin-4-yl)piperazin-1-yl)ethanol (16 mg, 0.062 mmol).

MS m/z: 541.06 [M+1].

Example 20

N-(3-(2-(3-methyl-4-oxo-3,4-dihydroquinazolin-7-ylamino)thieno[3,2-d]pyrimidin-7-yl)phenyl)methanesulfonamide

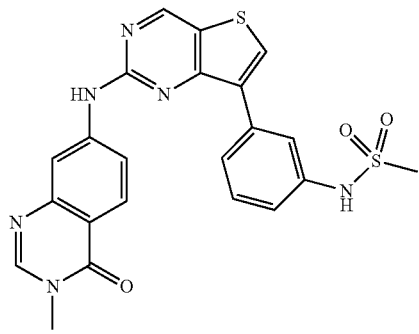 [SMILES: Cn1cnc2cc(Nc3ncc4scc(-c5cccc(NS(C)(=O)=O)c5)c4n3)ccc2c1=O]

N-(3-(2-(3-Methyl-4-oxo-3,4-dihydroquinazolin-7-ylamino)thieno[3,2-d]pyrimidin-7-yl)phenyl)methane sulfonamide was prepared in the same manner as Step 4 of Example 19 using 7-bromo-3-methylquinazolin-4(3H)-one.

MS m/z: 479.00 [M+1].

Example 21

N-(3-(2-(5-acetylthiophen-2-ylamino)thieno[3,2-d]pyrimidin-7-yl)phenyl)methanesulfonamide

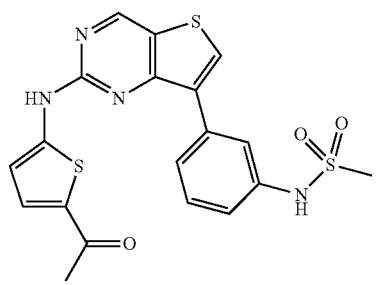 [SMILES: CC(=O)c1ccc(Nc2ncc3scc(-c4cccc(NS(C)(=O)=O)c4)c3n2)s1]

N-(3-(2-(5-acetylthiophen-2-ylamino)thieno[3,2-d]pyrimidin-7-yl)phenyl)methanesulfonamide was prepared in the same manner as Step 4 of Example 19 using 1-(5-bromothiophen-2-yl)ethanone.

MS m/z: 479.00 [M+1].

Example 22

7-(4-((4-ethylpiperazin-1-yl)methyl)phenyl)-N-(6-morpholinopyridin-3-yl)thieno[3,2-d]pyridin-2-amine The compound of Example 22 represented by the following structural formula was prepared by a 5-step synthesis process as follows.

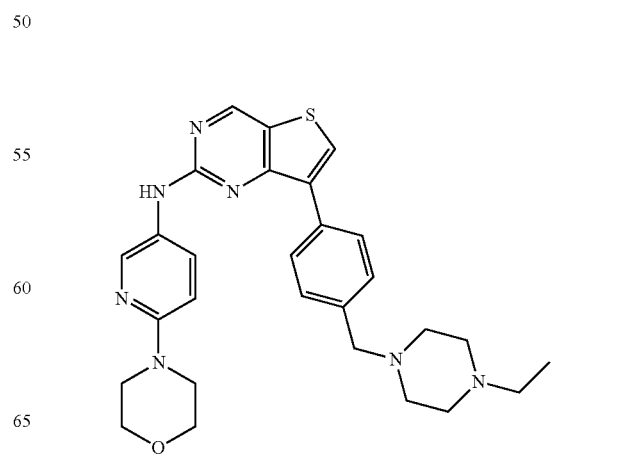

Step 1: ethyl 4-(2-chlorothieno[3,2-d]pyrimidin-7-yl)benzoate

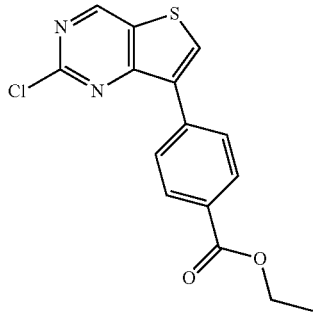 [SMILES: CCOC(=O)c1ccc(-c2csc3cnc(Cl)nc23)cc1]

Ethyl 4-(2-chlorothieno[3,2-d]pyrimidin-7-yl)benzoate (185 mg, 72% yield) was prepared in the same manner as Step 6 of Example 1 using 7-bromo-2-chlorothieno[3,2-d]pyrimidine (200 mg, 0.81 mmol) and 4-(ethoxycarbonyl)phenylboronic acid (157 mg, 0.81 mmol).

$^1$H NMR (400 MHz, DMSO-$d_6$) δ 9.56 (s, 1H), 8.98 (s, 1H), 8.17 (d, J=8.3 Hz, 2H), 8.09 (d, J=8.3 Hz, 2H), 4.35 (q, 2H), 1.24 (t, 3H), MS m/z: 319.49 [M+1].

Step 2: ethyl 4-(2-(6-morpholinopyridin-3-ylamino)thieno[3,2-d]pyrimidin-7-yl)benzoate

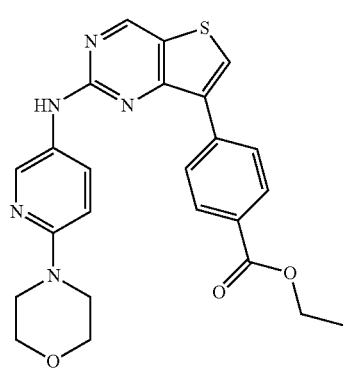 [SMILES: CCOC(=O)c1ccc(-c2csc3cnc(Nc4ccc(N5CCOCC5)nc4)nc23)cc1]

Ethyl 4-(2-(6-morpholinopyridin-3-ylamino)thieno[3,2-d]pyrimidin-7-yl)benzoate (160 mg, 61% yield) was prepared in the same manner as Step 10 of Example 1 using ethyl 4-(2-(6-morpholinopyridin-3-ylamino)thieno[3,2-d]pyrimidin-7-yl)benzoate (180 mg, 0.57 mmol) and 6-morpholinopyridin-3-amine (152 mg, 0.81 mmol).

$^1$H NMR (400 MHz, DMSO-$d_6$) δ 9.50 (s, 1H), 9.20 (s, 1H), 8.73 (s, 1H), 8.51 (d, 1H), 8.25 (d, 2H), 8.03 (d, 2H), 7.98 (d, 1H), 6.87 (d, 1H), 4.34 (q, 2H), 3.72 (m, 4H), 3.38 (m, 4H), 1.35 (t, 3H), MS m/z: 462.07 [M+1].

Step 3: (4-(2-(6-morpholinopyridin-3-ylamino)thieno[3,2-d]pyrimidin-7-yl)phenyl)methanol

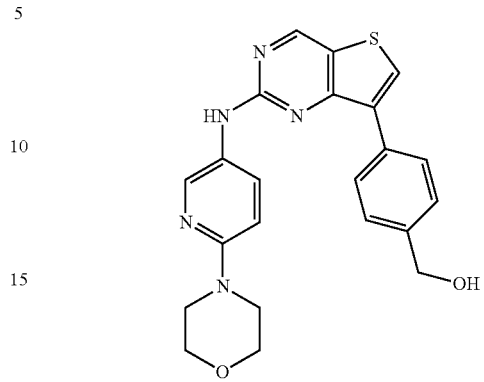

Ethyl 4-(2-(6-morpholinopyridin-3-ylamino)thieno[3,2-d]pyrimidin-7-yl)benzoate (150 mg, 0.33 mmol) was dissolved in anhydrous tetrahydrofuran (1.5 mL) and lithium aluminum hydride 2.0 M tetrahydrofuran (0.25 mL, 0.50 mmol) solution was slowly added at 0° C. The reaction mixture was stirred at room temperature for 2 hours. Upon completion of the reaction, the reaction mixture was diluted with ethyl ether (2.0 mL). The remaining lithium aluminum hydride was removed by adding water very slowly. After adding magnesium sulfate, the mixture was concentrated by filtering. The resultant target compound (130 mg, 95% yield) was used in the following reaction without purification.

$^1$H NMR (400 MHz, DMSO-$d_6$) δ 9.49 (s, 1H), 9.17 (s, 1H), 8.51 (s, 1H), 8.09 (s, 1H), 8.06 (d, 2H), 7.42 (d, 2H), 6.87 (d, 1H), 6.83 (d, 1H), 5.24 (t, 1H), 4.56 (d, 2H), 3.73 (m, 4H), 3.37 (m, 4H), MS m/z: 420.05 [M+1].

Step 4: 4-(2-(6-morpholinopyridin-3-ylamino)thieno[3,2-d]pyrimidin-7-yl)benzylmethanesulfonate

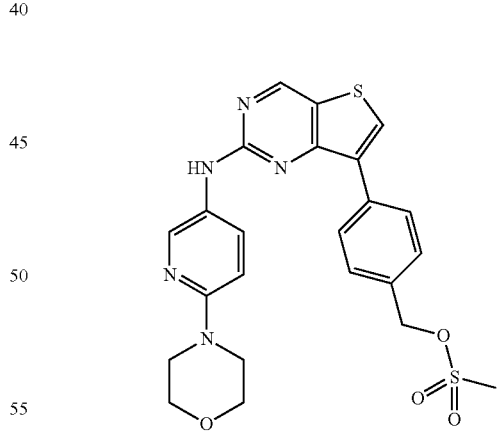

(4-(2-(6-Morpholinopyridin-3-ylamino)thieno[3,2-d]pyrimidin-7-yl)phenyl)methanol (120 mg, 0.28 mmol) was dissolved in anhydrous tetrahydrofuran (2 mL) and then methanesulfonyl chloride (27 μL, 0.34 mmol) and triethylamine (0.80 μL, 0.57 mmol) were added. The reaction mixture was stirred for 4 hours, diluted with ethyl acetate, and washed with brine. The organic layer was dried with magnesium sulfate, filtered with celite, and then concentrated. Purification by chromatography (50% ethyl acetate/hexane) yielded the target compound (128 mg, 89% yield).

¹H NMR (400 MHz, DMSO-d₆) δ 9.71 (s, 1H), 9.27 (s, 1H), 8.62 (s, 1H), 8.53 (s, 1H), 8.20 (d, 1H), 8.10 (d, 2H), 7.58 (d, 2H), 6.87 (s, 1H), 5.38 (s, 2H), 3.73 (m, 4H), 3.37 (m, 4H), 2.31 (s, 3H), MS m/z: 498.02 [M+1].

Step 5: 7-(4-((4-ethylpiperazin-1-yl)methyl)phenyl)-N-(6-morpholinopyridin-3-yl)thieno[3,2-d]pyrimidin-2-amine

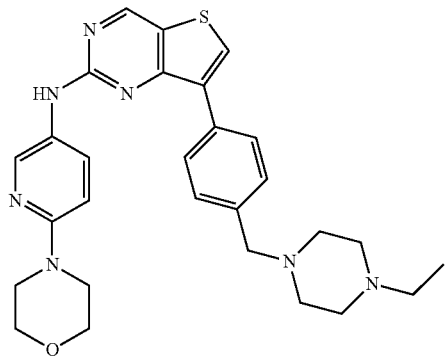 [SMILES: CCN1CCN(Cc2ccc(-c3csc4cnc(Nc5ccc(N6CCOCC6)nc5)nc34)cc2)CC1]

4-(2-(6-Morpholinopyridin-3-ylamino)thieno[3,2-d]pyrimidin-7-yl)benzylmethanesulfonate (30 mg, 0.06 mmol) was dissolved in N,N-dimethylformamide (1 mL) and potassium carbonate (17 mg, 0.12 mmol) and 1-ethylpiperazine (38 μL, 0.30 mmol) were added. The reaction mixture was stirred at 80° C. for a day, diluted with ethyl acetate, and washed with brine. The organic layer was dried with magnesium sulfate, filtered with celite, and then concentrated. Purification by chromatography (5% methanol/dichloromethane) yielded the target compound (22 mg, 70% yield).

¹H NMR (400 MHz, DMSO-d₆) δ 9.48 (s, 1H), 9.17 (s, 1H), 8.51 (s, 2H), 8.05 (d, 1H), 8.01 (d, 2H), 7.38 (d, 2H), 6.82 (d, 1H), 3.71 (m, 4H), 3.48 (s, 2H), 3.38 (m, 4H), 2.43-2.30 (m, 10H), 0.98 (t, 3H), MS m/z: 516.20 [M+1].

Example 23

N-(6-morpholinopyridin-3-yl)-7-(4-(piperidin-1-ylmethyl)phenyl)thieno[3,2-d]pyrimidin-2-amine

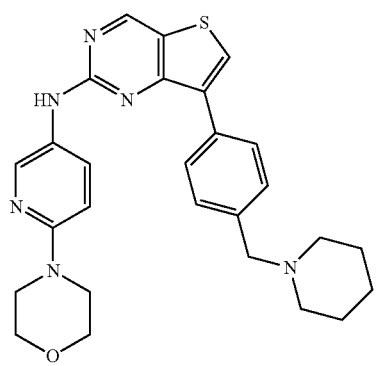 [SMILES: c1cc(-c2csc3cnc(Nc4ccc(N5CCOCC5)nc4)nc23)ccc1CN1CCCCC1]

N-(6-Morpholinopyridin-3-yl)-7-(4-(piperidin-1-ylmethyl)phenyl)thieno[3,2-d]pyrimidin-2-amine was prepared in the same manner as Step 5 of Example 22 using piperidine.

¹H NMR (400 MHz, DMSO-d₆) δ 9.47 (s, 1H), 9.16 (s, 1H), 8.51 (d, 1H), 8.50 (s, 1H), 8.04 (d, 1H), 8.00 (d, 2H), 7.38 (d, 2H), 6.82 (d, 1H), 3.71 (m, 4H), 3.47 (s, 2H), 3.37 (m, 4H), 2.35 (m, 4H), 1.49 (m, 4H), 1.39 (m, 2H). MS m/z: 487.16 [M+1].

Example 24

7-(4-(morpholinomethyl)phenyl)-N-(6-morpholinopyridin-3-yl)thieno[3,2-d]pyrimidin-2-amine

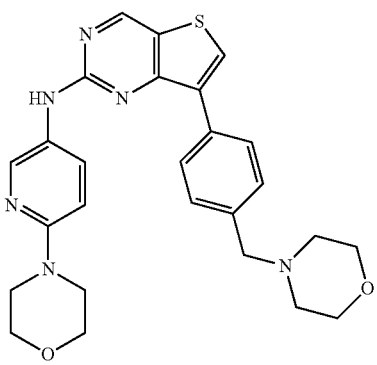 [SMILES: c1cc(-c2csc3cnc(Nc4ccc(N5CCOCC5)nc4)nc23)ccc1CN1CCOCC1]

7-(4-(Morpholinomethyl)phenyl)-N-(6-morpholinopyridin-3-yl)thieno[3,2-d]pyrimidin-2-amine was prepared in the same manner as Step 5 of Example 22 using morpholine.

MS m/z: 489.11 [M+1].

Example 25

N-cyclopropyl-3-(2-(6-(4-ethylpiperazin-1-yl)pyridin-3-ylamino)thieno[3,2-d]pyrimidin-7-yl)benzamide The compound of Example 25 represented by the following structural formula was prepared by a 3-step synthesis process as follows.

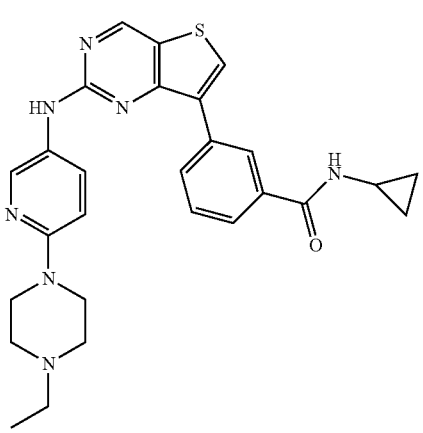 [SMILES: CCN1CCN(c2ccc(Nc3ncc4scc(-c5cccc(C(=O)NC6CC6)c5)c4n3)cn2)CC1]

Step 1:
3-(2-chlorothieno[3,2-d]pyrimidin-7-yl)benzoic acid

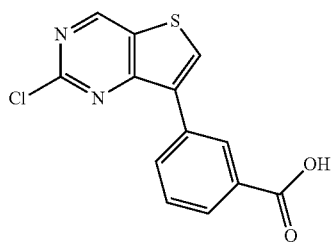 [SMILES: O=C(O)c1cccc(-c2csc3cnc(Cl)nc23)c1]

3-(2-Chlorothieno[3,2-d]pyrimidin-7-yl)benzoic acid (380 mg, 65% yield) was prepared in the same manner as Step 6 of Example 1 using 7-bromo-2-chlorothieno[3,2-d]pyrimidine (500 mg, 2.0 mmol) and 3-boronobenzoic acid (332 mg, 2.0 mmol).
MS m/z: 291.40 [M+1].

Step 2: 3-(2-chlorothieno[3,2-d]pyrimidin-7-yl)-N-cyclopropylbenzamide

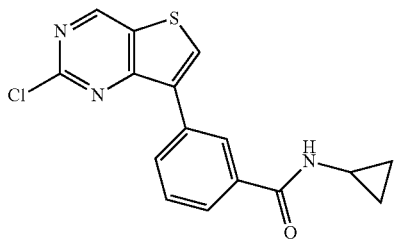 [SMILES: O=C(NC1CC1)c1cccc(-c2csc3cnc(Cl)nc23)c1]

3-(2-Chlorothieno[3,2-d]pyrimidin-7-yl)benzoic acid (600 mg, 2.06 mmol) was dissolved in N,N-dimethylformamide (20 mL) and then cyclopropylamine (234 mg, 4.12 mmol), 1-ethyl-3-(3-dimethylaminopropyl)carbodiimide (589 mg, 3.09 mmol), hydroxybenzotriazole (417 mg, 3.09 mmol) and trimethylamine (574 mL, 4.12 mmol) were added. The reaction mixture was stirred at room temperature for a day, diluted with ethyl acetate, and washed with ammonium chloride aqueous solution. The organic layer was dried with magnesium sulfate, filtered with celite, and then concentrated. Purification by chromatography (20% ethyl acetate/hexane) yielded the target compound (580 mg, 85% yield).
MS m/z: 330.54 [M+1].

Step 3: N-cyclopropyl-3-(2-(6-(4-ethylpiperazin-1-yl)pyridin-3-ylamino)thieno[3,2-d]pyrimidin-7-yl)benzamide

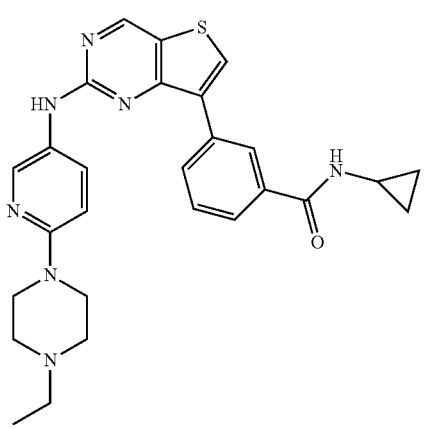 [SMILES: CCN1CCN(c2ccc(Nc3ncc4scc(-c5cccc(C(=O)NC6CC6)c5)c4n3)cn2)CC1]

N-Cyclopropyl-3-(2-(6-(4-ethylpiperazin-1-yl)pyridin-3-ylamino)thieno[3,2-d]pyrimidin-7-yl)benzamide (23 mg, 50% yield) was prepared in the same manner as Step 10 of Example 1 using 3-(2-chlorothieno[3,2-d]pyrimidin-7-yl)-N-cyclopropylbenzamide (30 mg, 0.09 mmol) and 6-(4-ethylpiperazin-1-yl)pyridin-3-amine (28 mg, 0.14 mmol).
$^1$H NMR (400 MHz, DMSO-$d_6$) δ 9.70 (s, 1H), 9.23 (s, 1H), 8.60 (s, 1H), 8.56 (d, J=2.6 Hz, 1H), 8.52 (d, J=4.2 Hz, 1H), 8.40 (s, 1H), 8.26 (m, 1H), 8.17 (d, J=7.8 Hz, 1H), 7.83 (d, J=7.8 Hz, 1H), 7.55 (t, 1H), 7.0 (d, J=9.4 Hz, 1H), 4.31 (m, 2H), 3.61 (m, 2H), 3.20 (m, 2H), 3.14 (m, 4H), 2.90 (m, 1H), 1.25 (t, 3H), 0.72 (m, 2H), 0.57 (m, 2H), MS m/z: 500.89 [M+1].

Example 26

N-cyclopropyl-3-(2-(6-methylpyridin-3-ylamino)thieno[3,2-d]pyrimidin-7-yl)benzamide

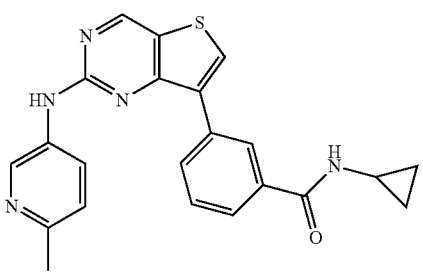 [SMILES: Cc1ccc(Nc2ncc3scc(-c4cccc(C(=O)NC5CC5)c4)c3n2)cn1]

N-Cyclopropyl-3-(2-(6-methylpyridin-3-ylamino)thieno[3,2-d]pyrimidin-7-yl)benzamide was prepared in the same manner as Step 10 of Example 1 using 6-methylpyridin-3-amine.
$^1$H NMR (400 MHz, DMSO-$d_6$) δ 9.84 (s, 1H), 9.27 (s, 1H), 8.71 (d, J=2.5 Hz, 1H), 8.61 (s, 1H), 8.51 (d, J=4.0 Hz, 1H), 8.39 (s, 1H), 8.34 (dd, J=2.3 Hz, J=8.2 Hz, 1H), 8.16 (d, J=7.7 Hz, 1H), 7.84 (d, J=7.8 Hz, 1H), 7.58 (t, 1H), 7.13 (d, J=8.4 Hz, 1H), 2.88 (m, 1H), 2.39 (s, 3H), 0.72 (m, 2H), 0.57 (m, 2H), MS m/z: 402.66 [M+1].

Example 27

N-cyclopropyl-3-(2-(6-morpholinopyridin-3-ylamino)thieno[3,2-d]pyrimidin-7-yl)benzamide

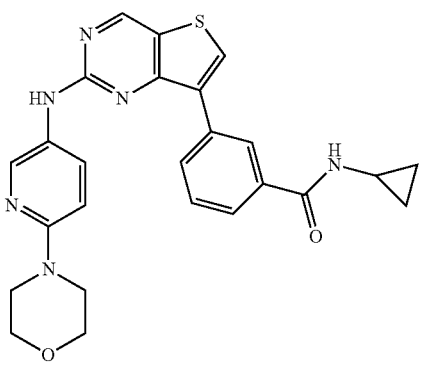 [SMILES: O=C(NC1CC1)c1cccc(-c2csc3cnc(Nc4ccc(N5CCOCC5)nc4)nc23)c1]

N-Cyclopropyl-3-(2-(6-morpholino pyridin-3-ylamino)thieno[3,2-d]pyrimidin-7-yl)benzamide was prepared in the same manner as Step 40 of Example 1 using 6-morpholinopyridin-3-amine.

¹H NMR (400 MHz, DMSO-d₆) δ 9.54 (s, 1H), 9.20 (s, 1H), 8.57 (s, 1H), 8.48 (d, J=4.4 Hz, 1H), 8.42 (d, J=2.7 Hz, 1H), 8.37 (s, 1H), 8.18 (m, 2H), 7.81 (m, 1H), 7.56 (t, 1H), 6.80 (d, J=9.0 Hz, 1H), 3.72 (m, 4H), 3.38 (m, 4H), 2.89 (m, 1H), 0.72 (m, 2H), 0.57 (m, 2H), MS m/z: 473.87 [M+1].

Example 28

N-cyclopropyl-3-(2-(6-(4-(2-hydroxyethyl)piperazin-1-yl)-2-methylpyrimidin-4-ylamino)thieno[3,2-d]pyrimidin-7-yl)benzamide The compound of Example 28 represented by the following structural formula was prepared by a 3-step synthesis process as follows.

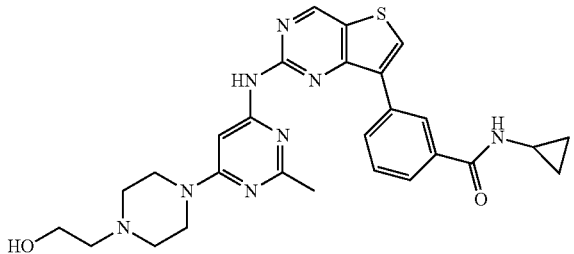 [SMILES: Cc1nc(Nc2ncc3scc(-c4cccc(C(=O)NC5CC5)c4)c3n2)cc(N2CCN(CCO)CC2)n1]

Step 1:
3-(2-aminothieno[3,2-d]pyrimidin-7-yl)benzoic acid

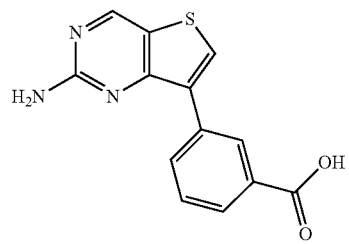 [SMILES: Nc1ncc2scc(-c3cccc(C(=O)O)c3)c2n1]

3-(2-Aminothieno[3,2-d]pyrimidin-7-yl)benzoic acid (800 mg, 56% yield) was prepared in the same manner as Step 6 of Example 1 using 7-bromothieno[3,2-d]pyrimidin-2-amine (1.2 g, 5.24 mmol) and 3-boronobenzoic acid (870 mg, 5.24 mmol).
MS m/z: 272.27 [M+1].

Step 2: 3-(2-aminothieno[3,2-d]pyrimidin-7-yl)-N-cyclopropylbenzamide

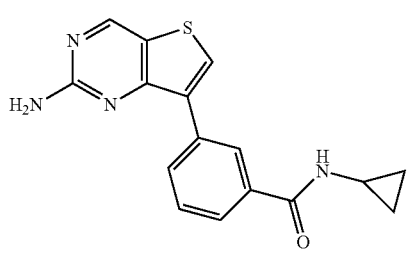 [SMILES: Nc1ncc2scc(-c3cccc(C(=O)NC4CC4)c3)c2n1]

3-(2-Aminothieno[3,2-d]pyrimidin-7-yl)-N-cyclopropylbenzamide (850 mg, 93% yield) was prepared in the same mariner as Step 2 of Example 25 using 3-(2-aminothieno[3,2-d]pyrimidin-7-yl)benzoic acid (800 mg, 2.95 mmol).
¹H NMR (400 MHz, DMSO-d₆) δ 8.57 (s, 1H), 8.15 (s, 1H), 7.84 (m, 2H), 7.55 (t, 1H), 7.20 (m, 1H), 2.88 (m, 1H), 0.72 (m, 2H), 0.58 (m, 2H), MS m/z: 311.37 [M+1].

Step 3: N-cyclopropyl-3-(2-(6-(4-(2-hydroxyethyl)piperazin-1-yl)-2-methylpyrimidin-4-ylamino)thieno[3,2-d]pyrimidin-7-yl)benzamide

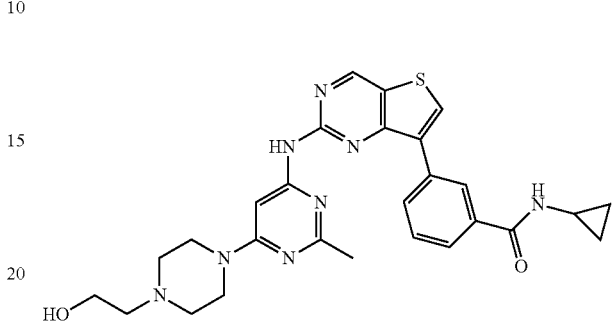

N-Cyclopropyl-3-(2-(6-(4-(2-hydroxyethyl)piperazin-1-yl)-2-methylpyrimidin-4-ylamino)thieno[3,2-d]pyrimidin-7-yl)benzamide (16 mg, 47% yield) was prepared in the same manner as Step 10 of Example 1 using 3-(2-aminothieno[3,2-d]pyrimidin-7-yl)-N-cyclopropylbenzamide (20 mg, 0.064 mmol) and 2-(4-(6-chloro-2-methylpyrimidin-4-yl)piperazin-1-yl)ethanol (17 mg, 0.064 mmol).
MS m/z: 531.20 [M+1].

Example 29

3-(2-(6-(4-(2-hydroxyethyl)piperazin-1-yl)-2-methylpyrimidin-4-ylamino)thieno[3,2-d]pyrimidin-7-yl)-N-methylbenzenesulfonamide The compound of Example 29 represented by the following structural formula was prepared by a 4-step synthesis process as follows.

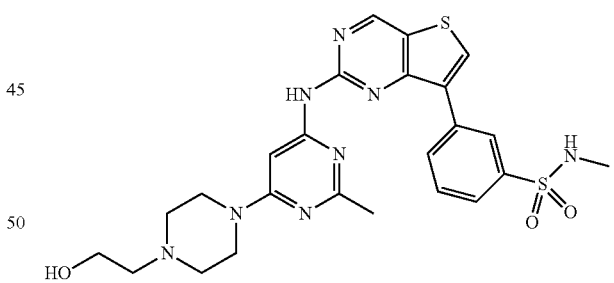

Step 1: 3-bromo-N-methylbenzenesulfonamide

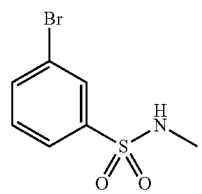

Methylamine hydrochloride (1057 mg, 15.65 mmol) and triethylamine (3.3 mL, 23.48 mmol) were dissolved in dichloromethane (20 mL) and then 3-bromobenzene-1-sulfonyl chloride (4.0 g, 15.65 mmol) was slowly added. The reaction mixture was stirred at room temperature for 2 hours, diluted with dichloromethane, and washed with brine. The organic layer was dried with magnesium sulfate, filtered with celite, and then concentrated. The resultant target compound (3.5 g, 90% yield) was used in the following reaction without purification.

MS m/2: 250.32, 252.30 [M+1].

Step 2: N-methyl-3-(4,4,5,5-tetramethyl-1,3,2-dioxaborolan-2-yl)benzenesulfonamide

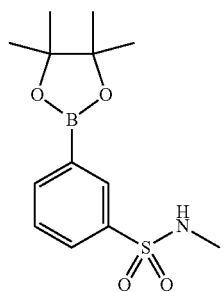

3-Bromo-N-methylbenzenesulfonamide (1.6 g, 6.39 mmol) was dissolved in anhydrous DMSO (21 mL) and then potassium acetate (1.57 g, 15.99 mmol) and bis(pinacolato)diboron (1.63 g, 6.39 mmol) were added. After flowing nitrogen to the reaction mixture for 10 minutes, Pd(dppf)$_2$Cl$_2$ (522 mg, 0.64 mmol) was added. The reaction mixture was stirred at 80° C. for 6 hours, diluted with ethyl acetate, and washed with brine. The organic layer was dried with magnesium sulfate, filtered with celite, and then concentrated. Purification by chromatography (10% ethyl acetate/hexane) yielded the target compound (1.65 g, 86% yield).

MS m/z: 298.52 [M+1].

Step 3: 3-(2-aminothieno[3,2-d]pyrimidin-7-yl)-N-methylbenzenesulfonamide

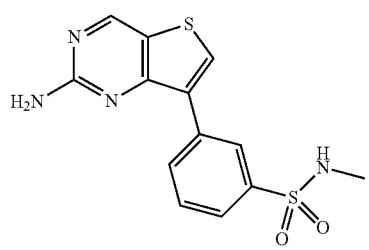 [SMILES: CNS(=O)(=O)c1cccc(-c2csc3cnc(N)nc23)c1]

3-(2-Aminothieno[3,2-d]pyrimidin-7-yl)-N-methylbenzenesulfonamide (180 mg, 64% yield) was prepared in the same manner as Step 6 of Example 1 using 7-bromothieno[3,2-d]pyrimidin-2-amine (200 mg, 0.87 mmol) and N-methyl-3-(4,4,5,5-tetramethyl-1,3,2-dioxaborolan-2-yl)benzenesulfonamide (260 mg, 0.87 mmol).

$^1$H NMR (400 MHz, DMSO-d$_6$) δ 9.03 (s, 1H), 8.58 (s, 1H), 8.43 (s, 1H), 8.36 (d, 1H), 7.77-7.54 (m, 3H), 6.58 (s, 2H), 2.40 (s, 3H), MS m/z: 321.05 [M+1].

Step 4: 3-(2-(6-(4-(2-hydroxyethyl)piperazin-1-yl)-2-methylpyrimidin-4-ylamino)thieno[3,2-d]pyrimidin-7-yl)-N-methylbenzenesulfonamide

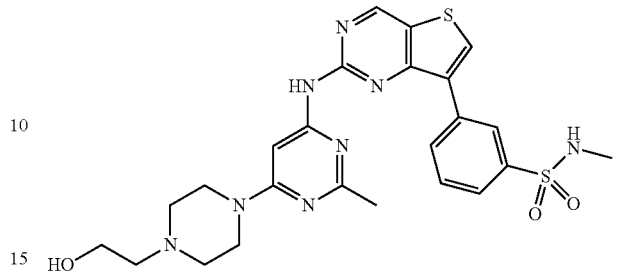

3-(2-(6-(4-(2-Hydroxyethyl)piperazin-1-yl)-2-methylpyrimidin-4-ylamino)thieno[3,2-d]pyrimidin-7-yl)-N-methylbenzenesulfonamide (18 mg, 53% yield) was prepared in the same manner as Step 10 of Example 1 using 3-(2-aminothieno[3,2-d]pyrimidin-7-yl)-N-methylbenzenesulfonamide (20 mg, 0.062 mmol) and 2-(4-(6-chloro-2-methylpyrimidin-4-yl)piperazin-1-yl)ethanol (17 mg, 0.062 mmol).

MS m/z: 541.24 [M+1].

Example 30

N-(6-(4-ethylpiperazin-1-yl)pyridin-3-yl)-7-(quinolin-3-yl)thieno[3,2-d]pyrimidin-2-amine The compound of Example 30 represented by the following structural formula was prepared by a 2-step synthesis process as follows.

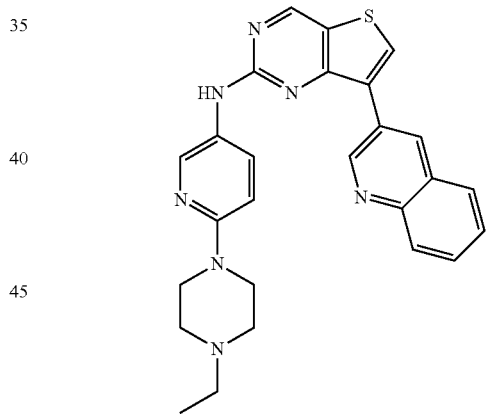

Step 1:
2-chloro-7-(quinolin-3-yl)thieno[3,2-d]pyrimidine

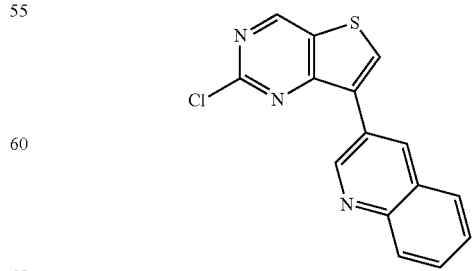

2-Chloro-7-(quinolin-3-yl)thieno[3,2-d]pyrimidine (140 mg, 58% yield) was prepared in the same manner as Step 6 of Example 1 using 7-bromo-2-chlorothieno[3,2-d]pyrimidine (200 mg, 0.81 mmol) and quinolin-3-ylboronic acid (140 mg, 0.81 mmol).

$^1$H NMR (400 MHz, DMSO-d$_6$) δ 9.63 (s, 1H), 9.48 (s, 1H), 9.14 (s, 1H), 8.96 (s, 1H), 8.10 (m, 1H), 7.85 (t, 1H), 7.69 (m, 1H), 2H), MS m/z: 298.46 [M+1].

Step 2: N-(6-(4-ethylpiperazin-1-yl)pyridin-3-yl)-7-(quinolin-3-yl)thieno[3,2-d]pyrimidin-2-amine

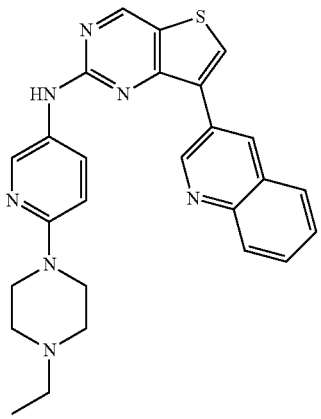 [SMILES: CCN1CCN(c2ccc(Nc3ncc4scc(-c5cnc6ccccc6c5)c4n3)cn2)CC1]

N-(6-(4-Ethylpiperazin-1-yl)pyridin-3-yl)-7-(quinolin-3-yl)thieno[3,2-d]pyrimidin-2-amine (32 mg, 67% yield) was prepared in the same manner as Step 10 of Example 1 using 2-chloro-7-(quinolin-3-yl)thieno[3,2-d]pyrimidine (30 mg, 0.10 mmol) and 6-(4-ethylpiperazin-1-yl)pyridin-3-amine (31 mg, 0.15 mmol).

$^1$H NMR (DMSO-d$_6$) δ 9.64 (s, 1H), 9.52 (d, J=1.9 Hz, 1H), 9.38 (s, 1H), 9.27 (s, 1H), 8.96 (s, 1H), 8.74 (m, 1H), 8.11 (m, 2H), 7.98 (dd, J=2.6 Hz, J=9.0 Hz, 1H), 7.84 (m, 1H), 7.71 (t, 1H), 7.02 (d, J=9.1 Hz, 1H), 4.38 (m, 2H), 3.64 (m, 2H), 3.20 (m, 2H), 3.07 (m, 4H), 1.27 (t, 3H), MS m/z: 468.80 [M+1].

Example 31

N-(6-methylpyridin-3-yl)-7-(quinolin-3-yl)thieno[3,2-d]pyrimidin-2-amine

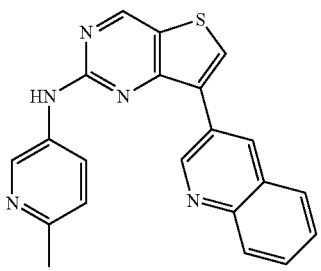 [SMILES: Cc1ccc(Nc2ncc3scc(-c4cnc5ccccc5c4)c3n2)cn1]

N-(6-Methyl pyridin-3-yl)-7-(quinolin-3-yl)thieno[3,2-d]pyrimidin-2-amine was prepared in the same manner as Step 2 of Example 30 using 6-methylpyridin-3-amine.

$^1$H NMR (DMSO-d$_6$) δ 9.86 (s, 1H), 9.51 (d, J=1.9 Hz, 1H), 9.32 (s, 1H), 9.21 (d, J=1.9 Hz, 1H), 8.93 (s, 1H), 8.89 (d, J=2.5 Hz, 1H), 8.17 (dd, J=2.5 Hz, J=8.4 Hz, 1H), 8.09 (m, 2H), 7.84 (m, 1H), 7.70 (t, 1H), 7.17 (d, J=8.4 Hz, 1H), 2.39 (s, 3H), MS m/z: 370.60 [M+1].

Example 32

N-(6-morpholinopyridin-3-yl)-7-(quinolin-3-yl)thieno[3,2-d]pyrimidin-2-amine

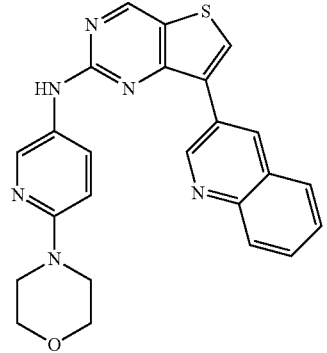 [SMILES: c1ccc2ncc(-c3csc4cnc(Nc5ccc(N6CCOCC6)nc5)nc34)cc2c1]

N-(6-morpholinopyridin-3-yl)-7-(quinolin-3-yl)thieno[3,2-d]pyrimidin-2-amine was prepared in the same manner as Step 2 of Example 30 using 6-morpholinopyridin-3-amine. MS m/z: 441.76 [M+1].

Example 33

N-(3-(2-(6-morpholinopyridin-3-ylamino)thieno[3,2-d]pyrimidin-7-yl)phenyl)cyclopropanecarboxamide The compound of Example 33 represented by the following structural formula was prepared by a 4-step synthesis process as follows.

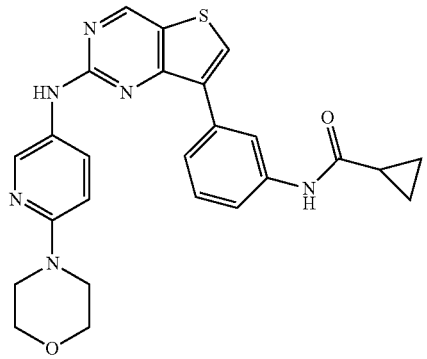 [SMILES: O=C(Nc1cccc(-c2csc3cnc(Nc4ccc(N5CCOCC5)nc4)nc23)c1)C1CC1]

Step 1:
2-chloro-7-(3-nitrophenyl)thieno[3,2-d]pyrimidine

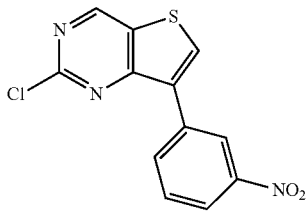 [SMILES: O=[N+]([O-])c1cccc(-c2csc3cnc(Cl)nc23)c1]

2-Chloro-7-(3-nitrophenyl)thieno[3,2-d]pyrimidine (430 mg, 73% yield) was prepared in the same manner as Step 6 of Example 1 using 7-bromo-2-chlorothieno[3,2-d]pyrimidine (500 mg, 2.02 mmol) and 3-nitrophenylboronic acid (337 mg, 2.02 mmol).

MS m/z: 292.03, 294.04 [M+1].

Step 2: N-(6-morpholinopyridin-3-yl)-7-(3-nitrophenyl)thieno[3,2-d]pyrimidin-2-amine

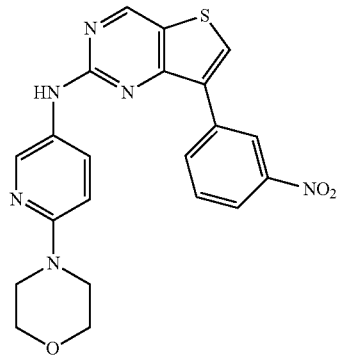 [SMILES: O=[N+]([O-])c1cccc(-c2csc3cnc(Nc4ccc(N5CCOCC5)nc4)nc23)c1]

N-(6-Morpholinopyridin-3-yl)-7-(3-nitrophenyl)thieno[3,2-d]pyrimidin-2-amine (480 mg, 78% yield) was prepared in the same manner as Step 10 of Example 1 using 2-chloro-7-(3-nitrophenyl)thieno[3,2-d]pyrimidine (400 mg, 1.37 mmol) and 6-morpholinopyridin-3-amine (369 mg, 2.06 mmol).

$^1$H NMR (DMSO-$d_6$) δ 9.68 (s, 1H), 9.15 (s, 1H), 8.93 (s, 1H), 8.81 (s, 1H), 8.49 (d, 1H), 8.43 (d, 1H), 8.23 (d, 1H), 8.08 (d, 1H), 7.86 (t, 1H), 6.78 (d, 1H), 3.70 (m, 4H), 3.38 (m, 4H), MS m/z: 435.08 [M+1].

Step 3: 7-(3-aminophenyl)-N-(6-morpholinopyridin-3-yl)thieno[3,2-d]pyrimidin-2-amine

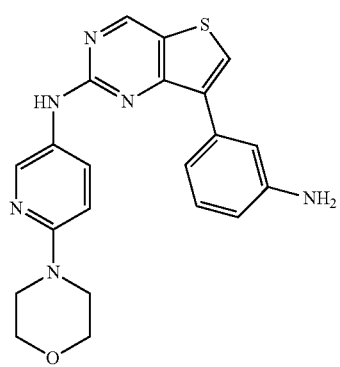 [SMILES: Nc1cccc(-c2csc3cnc(Nc4ccc(N5CCOCC5)nc4)nc23)c1]

N-(6-Morpholinopyridin-3-yl)-7-(3-nitro phenyl)thieno[3,2-d]pyrimidin-2-amine (476 mg, 1.10 mmol) was dissolved in ethanol (3.5 mL) and tin(II) chloride dihydrate (1238 mg, 5.48 mmol) was added. The reaction mixture was stirred at 80° C. for 2 hours. After removing ethanol by distillation under reduced pressure, ammonia water was slowly added to make pH 5. Sodium carbonate was added to thus prepared yellow precipitate until the pH reached 7. The precipitate was filtered and washed several times with ethyl acetate. The filtrate was concentrated and the resultant target compound (338 mg, 76%) was used without purification.

$^1$H NMR (DMSO-$d_6$) δ 9.51 (s, 1H), 9.20 (s, 1H), 8.60 (d, 1H), 8.37 (s, 1H), 8.07 (dd, 1H), 7.35 (s, 1H), 7.16 (d, 1H), 7.12 (d, 1H), 6.84 (d, 1H), 6.60 (d, 1H), 5.09 (s, 2H), 3.72 (m, 4H), 3.35 (m, 4H), MS m/z: 405.09 [M+1].

Step 4: N-(3-(2-(6-morpholinopyridin-3-ylamino)thieno[3,2-d]pyrimidin-7-yl)phenyl)cyclopropanecarboxamide

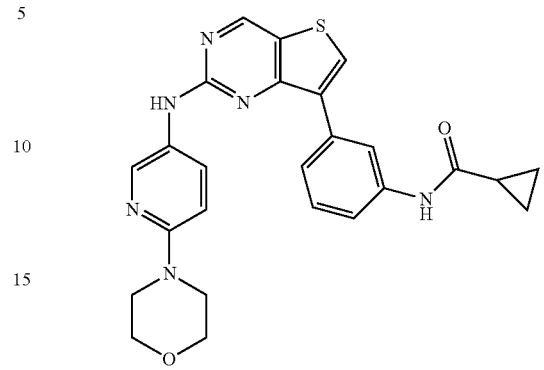

N-(3-(2-(6-Morpholinopyridin-3-ylamino)thieno[3,2-d]pyrimidin-7-yl)phenyl)cyclopropanecarboxamide (16 mg, 91% yield) was prepared in the same manner as Step 7 of Example 1 using 7-(3-aminophenyl)-N-(6-morpholino pyridin-3-yl)thieno[3,2-d]pyrimidin-2-amine (15 mg, 0.037 mmol) and cyclopropanecarbonyl chloride (5 mg, 0.044 mmol).

$^1$H NMR (DMSO-$d_6$) δ 10.30 (s, 1H), 9.51 (s, 1H), 9.18 (s, 1H), 8.68 (s, 1H), 8.41 (s, 1H), 8.02 (m, 2H), 7.66 (d, 1H), 7.57 (d, 1H), 7.41 (d, 1H), 6.85 (d, 1H), 3.70 (m, 4H), 3.38 (m, 4H), 2.19 (m, 1H), 0.96 (m, 2H), 0.80 (m, 2H). MS m/z: 473.09 [M+1].

Examples 34 to 41

The target compounds of Examples 34 to 41 were prepared through amidation reaction of the 7-(3-aminophenyl)-N-(6-morpholino pyridin-3-yl)thieno[3,2-d]pyrimidin-2-amine synthesized in Step 2 of Example 33 with various acyl chloride compounds. The procedure of amidation reaction is the same as Step 7 of Example 1.

Example 34

N-(3-(2-(6-morpholinopyridin-3-ylamino)thieno[3,2-d]pyrimidin-7-yl)phenyl)acetamide

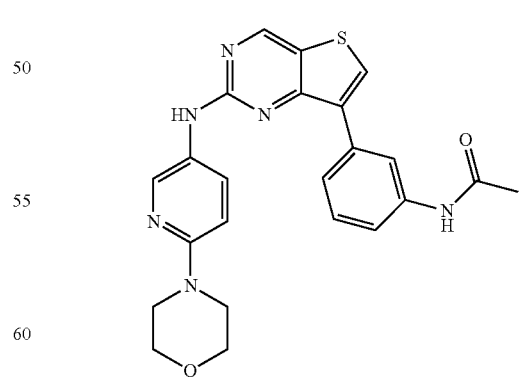

$^1$H NMR (DMSO-$d_6$) δ 10.02 (s, 1H), 9.51 (s, 1H), 9.18 (s, 1H), 8.51 (s, 1H), 8.41 (s, 1H), 8.13 (m, 2H), 7.66 (d, 1H), 7.59 (d, 1H), 7.41 (d, 1H), 6.76 (d, 1H), 3.70 (m, 4H), 3.38 (m, 4H), 2.07 (s, 3H), MS m/z: 447.06 [M+1].

Example 35

N-(3-(2-(6-morpholinopyridin-3-ylamino)thieno[3,2-d]pyrimidin-7-yl)phenyl)isopropylcarboxamide

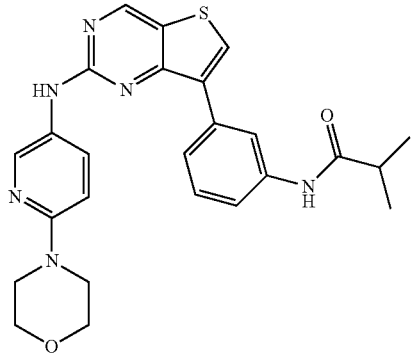 [SMILES: CC(C)C(=O)Nc1cccc(-c2csc3cnc(Nc4ccc(N5CCOCC5)nc4)nc23)c1]

MS m/z: 475.09 [M+1].

Example 36

4-chloro-N-(3-(2-(6-morpholinopyridin-3-ylamino)thieno[3,2-d]pyrimidin-7-yl)phenyl)-3-(trifluoromethyl)benzamide

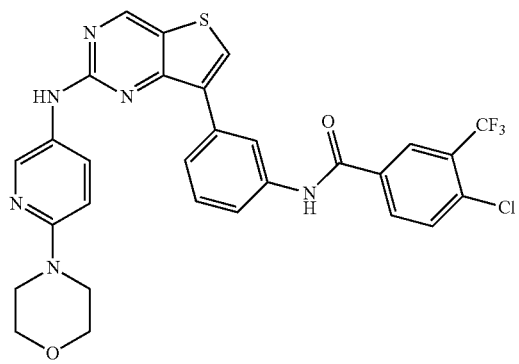 [SMILES: O=C(Nc1cccc(-c2csc3cnc(Nc4ccc(N5CCOCC5)nc4)nc23)c1)c1ccc(Cl)c(C(F)(F)F)c1]

MS m/z: 611.12 [M+1].

Example 37

N-(3-(2-(6-morpholinopyridin-3-ylamino)thieno[3,2-d]pyrimidin-7-yl)phenyl)ethanesulfonamide

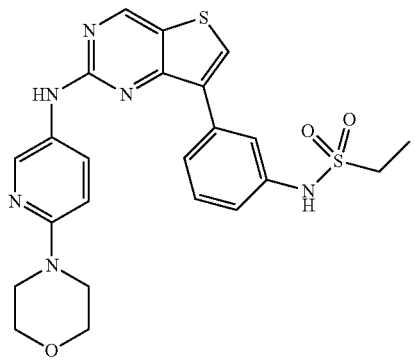 [SMILES: CCS(=O)(=O)Nc1cccc(-c2csc3cnc(Nc4ccc(N5CCOCC5)nc4)nc23)c1]

$^1$H NMR (DMSO-$d_6$) δ 9.88 (br, 1H), 9.51 (s, 1H), 9.22 (s, 1H), 8.47 (m, 2H), 8.17 (d, 1H), 7.78 (m, 2H), 7.45 (t, 1H), 7.21 (d, 1H), 6.87 (d, 1H), 3.71 (m, 4H), 3.38 (m, 4H), 3.14 (m, 2H), 1.19 (m, 3H), MS m/z: 497.04 [M+1].

Example 38

N-(3-(2-(6-morpholinopyridin-3-ylamino)thieno[3,2-d]pyrimidin-7-yl)phenyl)cyclopropanesulfonamide

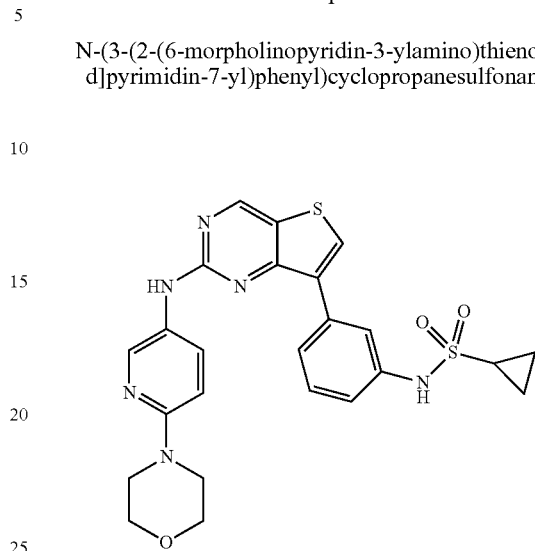

$^1$H NMR (DMSO-$d_6$) δ 9.76 (br, 1H), 9.50 (s, 1H), 9.18 (s, 1H), 8.47 (s, 1H), 8.38 (d, 1H), 8.20 (d, 1H), 7.79 (s, 1H), 7.49 (d, 2H), 7.45 (t, 1H), 6.86 (d, 1H), 3.71 (m, 4H), 3.38 (m, 4H), 2.69 (m, 1H), 0.96 (m, 2H), 0.80 (m, 2H), MS m/z: 509.05 [M+1].

Example 39

1-(4-chloro-3-(trifluoromethyl)phenyl)-3-(3-(2-(6-morpholinopyridin-3-ylamino)thieno[3,2-d]pyrimidin-7-yl)phenyl)urea

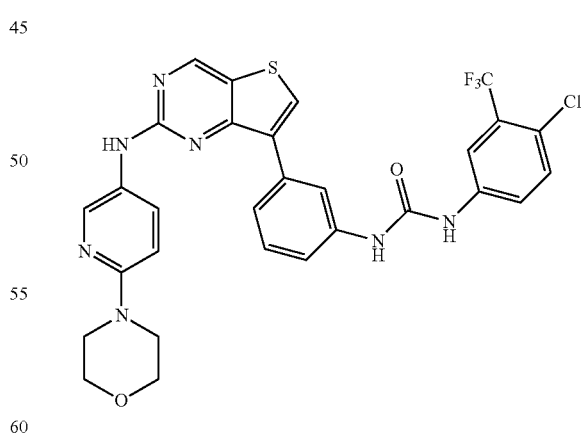

$^1$H NMR (DMSO-$d_6$) δ 9.51 (s, 1H), 9.17 (s, 1H), 8.45 (s, 1H), 8.38 (d, 1H), 8.23 (m, 2H), 8.17 (s, 1H), 7.70 (d, 1H), 7.58 (d, 1H), 7.48 (m, 2H), 7.37 (t, 1H), 6.72 (d, 1H), 3.70 (m, 4H), 3.38 (m, 4H), MS m/z: 626.09 [M+1].

Example 40

1-cyclohexyl-3-(3-(2-(6-morpholinopyridin-3-ylamino)thieno[3,2-d]pyrimidin-7-yl)phenyl)urea

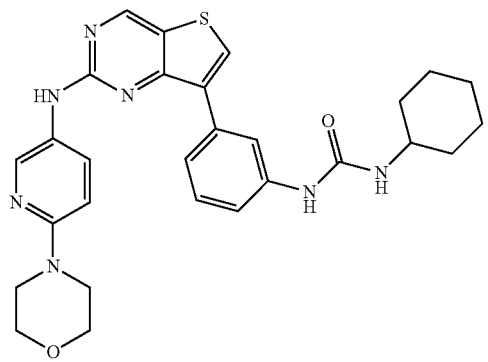 [SMILES: O=C(Nc1cccc(-c2csc3cnc(Nc4ccc(N5CCOCC5)nc4)nc23)c1)NC1CCCCC1]

MS m/z: 530.20 [M+1].

Example 41

1-(3-(2-(6-morpholinopyridin-3-ylamino)thieno[3,2-d]pyrimidin-7-yl)phenyl)-3-(2,2,2-trifluoroethyl)urea

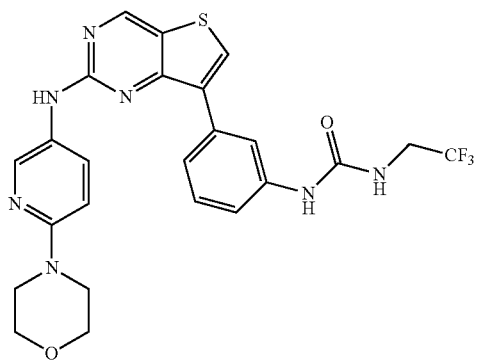 [SMILES: O=C(NCC(F)(F)F)Nc1cccc(-c2csc3cnc(Nc4ccc(N5CCOCC5)nc4)nc23)c1]

$^1$H NMR (DMSO-$d_6$) δ 9.51 (s, 1H), 9.17 (s, 1H), 8.45 (d, 1H), 8.42 (s, 1H), 7.92 (s, 1H), 7.59 (d, 1H), 7.49 (d, 1H), 7.36 (d, 1H), 7.14 (t, 1H), 6.76 (d, 1H), 3.92 (m, 2H), 3.71 (m, 4H), 3.38 (m, 4H), MS m/z: 530.10 [M+1].

Example 42

N-(6-(4-ethylpiperazin-1-yl)pyridin-3-yl)-7-(2-(trifluoromethyl)phenyl)thieno[3,2-d]pyrimidin-2-amine The compound of Example 42 represented by the following structural formula was prepared by a 2-step synthesis process as follows.

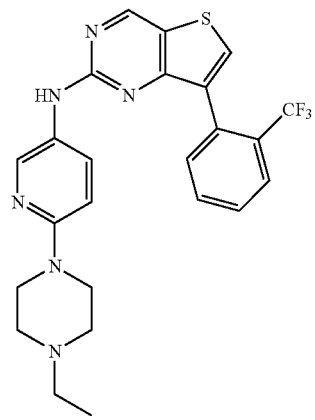 [SMILES: CCN1CCN(c2ccc(Nc3ncc4scc(-c5ccccc5C(F)(F)F)c4n3)cn2)CC1]

Step 1: 2-chloro-7-(2-(trifluoromethyl)phenyl)thieno[3,2-d]pyrimidine

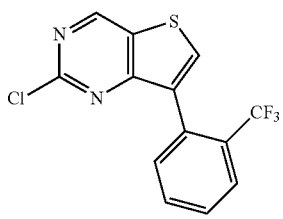 [SMILES: FC(F)(F)c1ccccc1-c1csc2cnc(Cl)nc12]

2-Chloro-7-(2-(trifluoromethyl)phenyl)thieno[3,2-d]pyrimidine (430 mg, 73% yield) was prepared in the same manner as Step 6 of Example 1 using 7-bromo-2-chloro thieno[3,2-d]pyrimidine (500 mg, 2.02 mmol) and 3-nitrophenylboronic acid (337 mg, 2.02 mmol).
$^1$H NMR (400 MHz, CDCl$_3$) δ 9.19 (s, 1H), 8.06 (s, 1H), 7.78 (m, 1H), 7.61 (m, 2H), 7.25 (m, 1H).

Step 2: N-(6-(4-ethylpiperazin-1-yl)pyridin-3-yl)-7-(2-(trifluoromethyl)phenyl)thieno[3,2-d]pyrimidin-2-amine

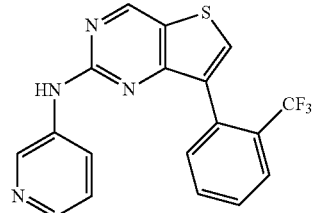
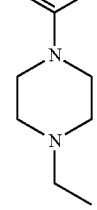

N-(6-(4-Ethylpiperazin-1-yl)pyridin-3-yl)-7-(2-(trifluoromethyl)phenyl)thieno[3,2-d]pyrimidin-2-amine (19 mg, 61% yield) was prepared in the same manner as Step 10 of Example 1 using 2-chloro-7-(2-(trifluoromethyl)phenyl)thieno[3,2-d]pyrimidine (20 mg, 0.64 mmol) and 6-(4-ethylpiperazin-1-yl)pyridin-3-amine (13 mg, 0.064 mmol).

MS m/z: 485.12 [M+1].

Example 43

N-(6-morpholinopyridin-3-yl)-7-(2-(trifluoromethyl)phenyl)thieno[3,2-d]pyrimidin-2-amine

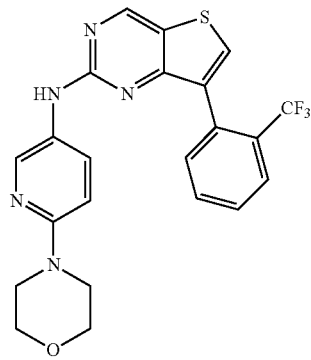 [SMILES: FC(F)(F)c1ccccc1-c1csc2cnc(Nc3ccc(N4CCOCC4)nc3)nc12]

N-(6-Morpholino pyridin-3-yl)-7-(2-(trifluoromethyl)phenyl)thieno[3,2-d]pyrimidin-2-amine was prepared in the same manner as Step 2 of Example 42 using 6-morpholinopyridin-3-amine.

MS m/z: 458.09 [M+1].

Example 44

N-(3-(2-(6-(4-ethylpiperazin-1-yl)pyridin-3-ylamino)thieno[3,2-d]pyrimidin-7-yl)phenyl)-N-methylmethanesulfonamide The compound of Example 44 represented by the following structural formula was prepared by a 2-step synthesis process as follows.

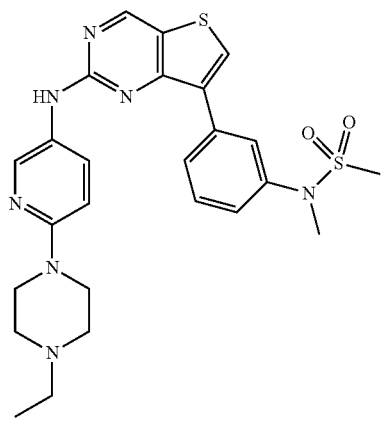 [SMILES: CCN1CCN(c2ccc(Nc3ncc4scc(-c5cccc(N(C)S(C)(=O)=O)c5)c4n3)cn2)CC1]

Step 1: N-(3-(2-chlorothieno[3,2-d]pyrimidin-7-yl)phenyl)-N-methylmethanesulfonamide

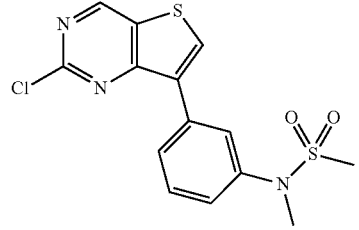 [SMILES: CN(c1cccc(-c2csc3cnc(Cl)nc23)c1)S(C)(=O)=O]

N-(3-(2-Chlorothieno[3,2-d]pyrimidin-7-yl)phenyl)methanesulfonamide (200 mg, 0.59 mmol) was dissolved in N,N-dimethylformamide (2.5 mL) and sodium hydride (36 mg, 0.89 mmol) was slowly added at 0° C. 10 minutes later, after adding iodomethane (100 mg, 0.71 mmol), the reaction mixture was stirred for an hour, diluted with ethyl acetate, and washed with brine. The organic layer was dried with magnesium sulfate, filtered, and then concentrated. The target compound (195 mg, 94% yield) was obtained without purification.

MS m/z: 354.03 [M+1].

Step 2: N-(3-(2-(6-(4-ethylpiperazin-1-yl)pyridin-3-ylamino)thieno[3,2-d]pyrimidin-7-yl)phenyl)-N-methylmethanesulfonamide

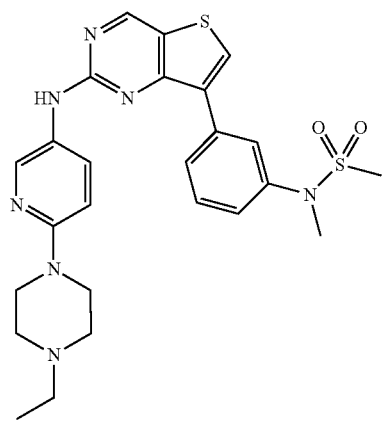 [SMILES: CCN1CCN(c2ccc(Nc3ncc4scc(-c5cccc(N(C)S(C)(=O)=O)c5)c4n3)cn2)CC1]

N-(3-(2-(6-(4-Ethylpiperazin-1-yl)pyridin-3-ylamino)thieno[3,2-d]pyrimidin-7-yl)phenyl)-N-methylmethanesulfonamide (19 mg, 64% yield) was prepared in the same manner as Step 10 of Example 1 using N-(3-(2-chlorothieno[3,2-d]pyrimidin-7-yl)phenyl)-N-methylmethanesulfonamide (20 mg, 0.57 mmol) and 6-(4-ethylpiperazin-1-yl)pyridin-3-amine (18 mg, 0.085 mmol).

MS m/z: 524.25 [M+1].

Example 45

N-methyl-N-(3-(2-(6-methylpyridin-3-ylamino)thieno[3,2-d]pyrimidin-7-yl)phenyl)methanesulfonamide

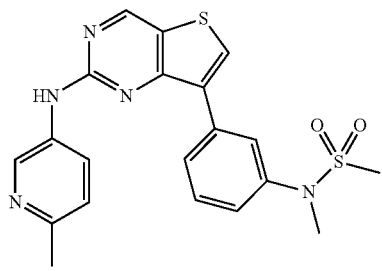 [SMILES: Cc1ccc(Nc2ncc3scc(-c4cccc(N(C)S(C)(=O)=O)c4)c3n2)cn1]

N-methyl-N-(3-(2-(6-methylpyridin-3-ylamino)thieno[3,2-d]pyrimidin-7-yl)phenyl)methanesulfonamide was prepared in the same manner as Step 2 of Example 44 using 6-methylpyridin-3-amine.

MS m/z: 426.11 [M+1].

Example 46

N-methyl-N-(3-(2-(6-morpholinopyridin-3-ylamino)thieno[3,2-d]pyrimidin-7-yl)phenyl)methanesulfonamide

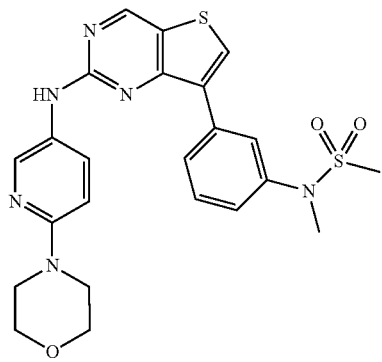 [SMILES: CN(c1cccc(-c2csc3cnc(Nc4ccc(N5CCOCC5)nc4)nc23)c1)S(C)(=O)=O]

N-Methyl-N-(3-(2-(6-morpholinopyridin-3-ylamino)thieno[3,2-d]pyrimidin-7-yl)phenyl)methanesulfonamide was prepared in the same manner as Step 2 of Example 44 using 6-morpholinopyridin-3-amine.

MS m/z: 497.18 [M+1].

Example 47

$N^2$-(6-morpholinopyridin-3-yl)-$N^7$-(3,4,5-trimethoxyphenyl)thieno[3,2-d]pyrimidin-2,7-diamine The compound of Example 47 represented by the following structural formula was prepared by a 2-step synthesis process as follows.

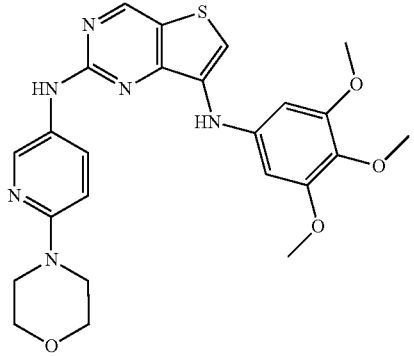 [SMILES: COc1cc(Nc2csc3cnc(Nc4ccc(N5CCOCC5)nc4)nc23)cc(OC)c1OC]

Step 1: 2-chloro-N-(3,4,5-trimethoxyphenyl)thieno[3,2-d]pyrimidin-7-amine

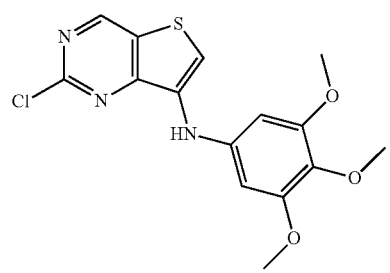 [SMILES: COc1cc(Nc2csc3cnc(Cl)nc23)cc(OC)c1OC]

7-Bromo-2-chlorothieno[3,2-d]pyrimidine (200 mg, 0.81 mmol) was dissolved in 2-butanol (4 mL) and then potassium carbonate (223 mg, 1.61 mmol) and 3,4,5-trimethoxybenzenamine (110 mg, 0.81 mmol) were added. After blowing nitrogen to the reaction mixture for 10 minutes, $Pd_2(dba)_3$ (50 mg, 0.048 mmol) and Xphos (35 mg, 0.073 mmol) were added. The reaction mixture was stirred at 80° C. for 2.5 hours and then filtered with celite. The filtrate was diluted with ethyl acetate and washed with brine. The organic layer was dried with magnesium sulfate, filtered with celite, and then concentrated. Purification by chromatography (15% ethyl acetate/hexane) yielded the target compound (120 mg, 43% yield).

$^1$H NMR (300 MHz, DMSO-$d_6$) δ 9.42 (s, 1H), 8.33 (s, 1H), 7.85 (s, 1H), 6.65 (s, 2H), 3.76 (s, 6H), 3.60 (s, 3H), MS m/z: 352.45 [M+1].

Step 2: $N^2$-(6-morpholinopyridin-3-yl)-$N^7$-(3,4,5-trimethoxyphenyl)thieno[3,2-d]pyrimidin-2,7-diamine

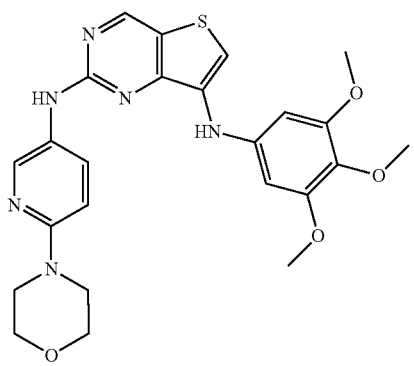 [SMILES: COc1cc(Nc2csc3cnc(Nc4ccc(N5CCOCC5)nc4)nc23)cc(OC)c1OC]

$N^2$-(6-Morpholinopyridin-3-yl)-$N^7$-(3,4,5-trimethoxyphenyl)thieno[3,2-d]pyrimidin-2,7-diamine (21 mg, 74% yield) was prepared in the same manner as Step 10 of Example 1 using 2-chloro-N-(3,4,5-trimethoxyphenyl)thieno[3,2-d]pyrimidin-7-amine (20 mg, 0.057 mmol) and 6-morpholinopyridin-3-amine (12 mg, 0.068 mmol).

MS m/z: 495.91 [M+1].

Example 48

N$^7$-methyl-N$^2$-(6-morpholino pyridin-3-yl)-N$^7$-(3,4,5-trimethoxyphenyl)thieno[3,2-d]pyrimidin-2,7-diamine The compound of Example 48 represented by the following structural formula was prepared by a 2-step synthesis process as follows.

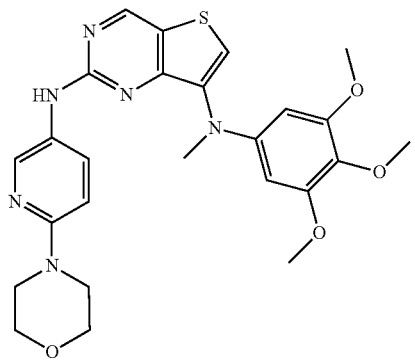 [SMILES: COc1cc(N(C)c2csc3cnc(Nc4ccc(N5CCOCC5)nc4)nc23)cc(OC)c1OC]

Step 1: 2-chloro-N-methyl-N-(3,4,5-trimethoxyphenyl)thieno[3,2-d]pyrimidin-7-amine

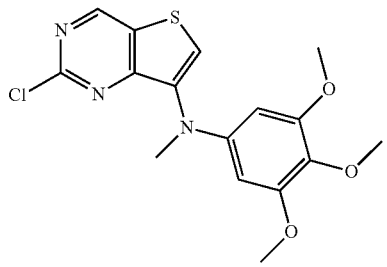 [SMILES: COc1cc(N(C)c2csc3cnc(Cl)nc23)cc(OC)c1OC]

2-Chloro-N-(3,4,5-trimethoxyphenyl)thieno[3,2-d]pyrimidin-7-amine (30 mg, 0.085 mmol) was dissolved in N,N-dimethylformamide (1 mL) and sodium hydride (5.2 mg, 0.13 mmol) was added at 0° C. After stirring for 10 minutes and adding iodomethane (15 mg, 0.10 mmol), the mixture was stirred for an hour, diluted with ethyl acetate, and washed with brine. The organic layer was dried with magnesium sulfate, filtered with celite, and then concentrated. The target compound (28 mg, 89% yield) was obtained without purification.

MS m/z: 366.05 [M+1].

Step 2: N$^7$-methyl-N$^2$-(6-morpholine pyridin-3-yl)-N$^7$-(3,4,5-trimethoxyphenyl)thieno[3,2-d]pyrimidin-2,7-diamine

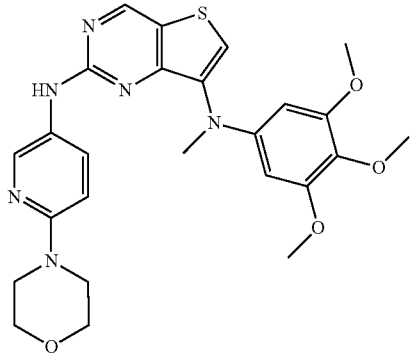 [SMILES: COc1cc(N(C)c2csc3cnc(Nc4ccc(N5CCOCC5)nc4)nc23)cc(OC)c1OC]

N$^7$-Methyl-N$^2$-(6-morpholinopyridin-3-yl)-N$^7$-(3,4,5-trimethoxyphenyl)thieno[3,2-d]pyrimidin-2,7-diamine (16 mg, 76% yield) was prepared in the same manner as Step of Example 1 using 2-chloro-N-methyl-N-(3,4,5-trimethoxyphenyl)thieno[3,2-d]pyrimidin-7-amine (15 mg, 0.041 mmol) and 6-morpholinopyridin-3-amine (9 mg, 0.049 mmol).

MS m/z: 509.16 [M+1].

Example 49

7-(3-(1,1-dioxido-2-isothiadiazolidinyl)phenyl)-N-(6-(4-ethylpiperazin-1-yl)pyridin-3-yl)thieno[3,2-d]pyrimidin-2-amine The compound of Example 49 represented by the following structural formula was prepared by a 3-step synthesis process as follows.

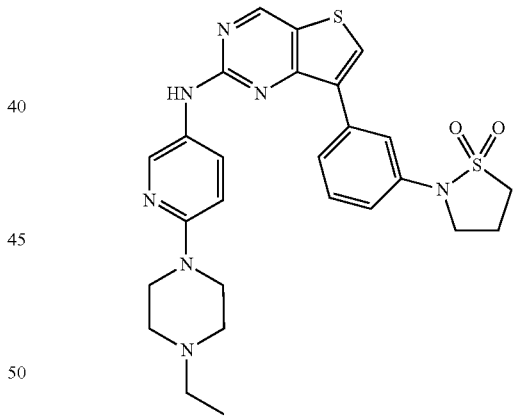

Step 1: 3-chloro-N-(3-(2-chlorothieno[3,2-d]pyrimidin-7-yl)phenyl)propane-1-sulfonamide

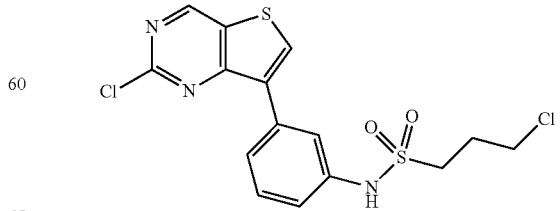

3-Chloro-N-(3-(2-chloro thieno[3,2-d]pyrimidin-7-yl)phenyl)propane-1-sulfonamide (240 mg, 78% yield) was prepared in the same manner as Step 7 of Example 1 using 3-(2-chlorothieno[3,2-d]pyrimidin-7-yl)benzenamine (200 mg, 0.76 mmol) and 3-chloropropane-1-sulfonyl chloride (145 mg, 0.84 mmol).

MS m/z: 402.26, 404.27 [M+1].

Step 2: 2-chloro-7-(3-(1,1-dioxido-2-isothiadiazolidinyl)phenyl)thieno[3,2-d]pyrimidine

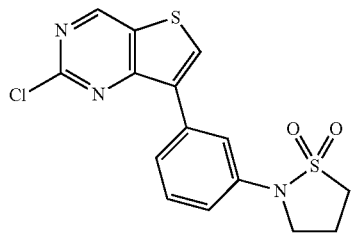 [SMILES: O=S1(=O)CCCN1c1cccc(-c2csc3cnc(Cl)nc23)c1]

3-Chloro-N-(3-(2-chloro thieno[3,2-d]pyrimidin-7-yl)phenyl)propane-1-sulfonamide (200 mg, 0.50 mmol) was dissolved in N,N-dimethylformamide (2.5 mL) and sodium hydride (24 mg, 0.60 mmol) was added at 0° C. After stirring for 4 hours, the mixture was diluted with ethyl acetate and washed with brine. The organic layer was dried with magnesium sulfate, filtered with celite, and then concentrated. The target compound (130 mg, 72% yield) was obtained without purification.

MS m/z: 366.13 [M+1].

Step 3: 7-(3-(1,1-dioxido-2-isothiadiazolidinyl)phenyl)-N-(6-(4-ethylpiperazin-1-yl)pyridin-3-yl)thieno[3,2-d]pyrimidin-2-amine

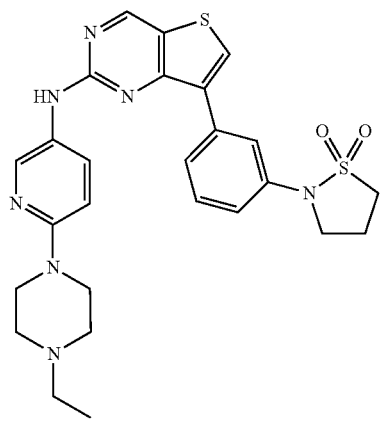 [SMILES: CCN1CCN(c2ccc(Nc3ncc4scc(-c5cccc(N6CCCS6(=O)=O)c5)c4n3)cn2)CC1]

7-(3-(1,1-Dioxido-2-isothiadiazolidinyl)phenyl)-N-(6-(4-ethylpiperazin-1-yl)pyridin-3-yl)thieno[3,2-d]pyrimidin-2-amine (15 mg, 51% yield) was prepared in the same manner as Step 10 of Example 1 using 2-chloro-7-(3-(1,1-dioxido-2-isothiadiazolidinyl)phenyl)thieno[3,2-d]pyrimidine (20 mg, 0.55 mmol) and 6-(4-ethylpiperazin-1-yl)pyridin-3-amine (17 mg, 0.082 mmol).

MS m/z: 536.96 [M+1].

The following example is an example of preparing a pharmaceutically acceptable salt of the compound represented by Chemical Formula 1. However, the scope of the present invention is not limited by the specific example.

Example 50

N-(3-(2-(6-(4-ethylpiperazin-1-yl)pyridin-3-ylamino)thieno[3,2-d]pyrimidin-7-yl)phenyl)methanesulfonamide hydrochloride

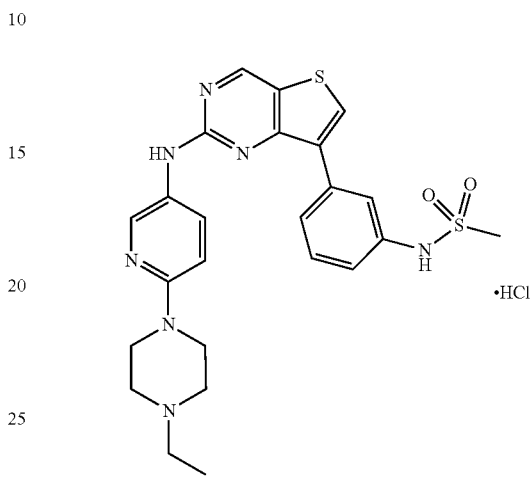

N-(3-(2-(6-(4-Ethylpiperazin-1-yl)pyridin-3-ylamino)thieno[3,2-d]pyrimidin-7-yl)phenyl)methanesulfonamide (300 mg, 0.589 mmol) was dissolved in tetrahydrofuran (5 mL) and then 4 M hydrogen chloride (147 µL) dissolved in dioxane was added at room temperature. 30 minutes later, thus prepared precipitate was filtered and dried at room temperature. The target compound N-(3-(2-(6-(4-ethylpiperazin-1-yl)pyridin-3-ylamino)thieno[3,2-d]pyrimidin-7-yl)phenyl)methanesulfonamide hydrochloride (305 mg) was yielded.

The novel compound represented by Chemical Formula 1 may be prepared into various formulations depending on purposes. The following examples illustrate some formulation comprising the compound represented by Chemical Formula 1 as an active ingredient, but they do not limit the present invention.

FORMULATION EXAMPLES

Formulation Example 1

Tablet (Direct Compression)

The active ingredient (5.0 mg) was sieved, mixed with lactose (14.1 mg), crospovidone USNF (0.8 mg) and magnesium stearate (0.1 mg), and then compressed into a tablet.

Formulation Example 2

Tablet (Wet Granulation)

The active ingredient (5.0 mg) was sieved and mixed with lactose (16.0 mg) and starch (4.0 mg). An adequate amount of the resulting solution was added to Polysorbate 80 (0.3 mg) dissolved in pure water, and then formed into granules. After drying, the granules were sieved and mixed with colloidal silicon dioxide (2.7 mg) and magnesium stearate (2.0 mg). The granules were compressed into a tablet.

Formulation Example 3

Powder and Capsule

The active ingredient (5.0 mg) was sieved and mixed with lactose (14.8 mg), polyvinylpyrrolidone (10.0 mg) and magnesium stearate (0.2 mg). The mixture was filled in a hard No. 5 gelatin capsule using an adequate apparatus.

Formulation Example 4

Injection

The active ingredient (100 mg) was mixed with mannitol (180 mg), $Na_2HPO_4 \cdot 12H_2O$ (26 mg) and distilled water (2974 mg) to prepare an injection.

TEST EXAMPLES

Test Example 1

Measurement of FAK Kinase Activity (ULight-LANCE Assay)

Full sequence FAK was purchased from Cell Signaling (Catalog No.: 7796). ULight-poly GT (PerkinElmer #TRF0100-D), Eu-anti-phospho-Tyr (PT66) (PerkinElmer #AD0068) and Lance detection buffer (PerkinElmer #CR-97-100) were purchased from PerkinElmer. The kinase solution (50 mM Tris-HCl pH 7.5, 10 mM $MgCl_2$, 1 mM EGTA, 2 mM DTT, 0.01% Tween-20) was adjusted to a final concentration of 3 nM by adding FAK diluted to 6 nM (2×) in white 384 OptiPlate, and added with an amount of 5 µL. 4×ULight-poly GT was adjusted to a final concentration of 100 nM. ATP (Sigma #A2383) was adjusted to a final concentration of 10 µM and in 2.5 µL aliquots. The test compound was sequentially diluted at 12 concentrations and treated with an amount of 0.5 µL. After shaking well and allowing to react at room temperature for 60 minutes, 5 µL of ethylenediaminetetraacetic acid (EDTA, final concentration 40 mM) diluted in Lance detection buffer (Lance detection buffer) was added and the mixture was left at room temperature for 5 minutes to stop the reaction. After adding 4×Eu-anti-phospho-Tyr (PT66) phosphorylated antibody diluted to a final concentration of 2 nM in detection buffer with an amount of 5 µL, and reaction was performed at room temperature for 60 minutes. After adjusting to detect time-resolved fluorescence energy transfer (TR-FRET) at excitation wavelength 320 nm and emission wavelength 665 nm, signals were detected using EnVision Multilabel Reader.

The FAK inhibition activity of the compounds represented by Chemical Formula 1 was measured. $IC_{50}$ ranged from 0.025 µM to 20 µM. FAK inhibition activity of some typical compounds according to the present invention is given in Table 1

TABLE 1

| Test compounds | FAK inhibition activity ($IC_{50}$, µM) |
|---|---|
| Example 1 | <0.5 |
| Example 11 | <1 |
| Example 12 | <1 |
| Example 13 | <0.5 |
| Example 25 | <0.5 |
| Example 26 | <10 |
| Example 27 | <0.5 |
| Example 30 | <0.5 |

Test Example 2

Measurement of Inhibition Activity Against Proliferation of HT-29 Human Colon Adenocarcinoma Cells HT-29 human colon adenocarcinoma cells were cultured in DMEM [10% FBS, 1% penicillin/streptomycin] at 37° C. in the presence of 5% $CO_2$. The cultured HT-29 cells were harvested with 0.05% trypsin-0.02% EDTA and seeded in a 96-well plate at $5 \times 10^3$ cells per well.

3-(4,5-Dimethylthiazol-2-yl)-2,5-diphenyltetrazolium bromide (MTT) assay (CellTiter 96 Assay, Promega) was employed to measure cell viability. After adding 15 µL of a dye per well and culturing for 2 hours, the cells were treated with 100 µL of a stop solution and absorbance was measured 24 hours later. The test compound was treated a day after plating. The test compound had been sequentially diluted at 12 concentrations from a 10 mM stock solution using sterilized dimethylsulfoxide (DMSO) and treated with an amount of 0.5 µL. Absorbance at 590 nm was recorded using EnVision2103, and GI50 value was calculated using GraphPad Prism 4.0 software.

The compounds represented by Chemical Formula 1 exhibited inhibition activity against proliferation of the HT-29 human colon adenocarcinoma cells. $GI_{50}$ ranged from 0.1 µM to 20 µM. The inhibition activity against proliferation of the HT-29 human colon adenocarcinoma cells of some typical compounds according to the present invention is given in Table 2.

TABLE 2

| Test compounds | Inhibition activity against proliferation of HT-29 cells ($GI_{50}$, µM) |
|---|---|
| Example 1 | <1 |
| Example 11 | <1 |
| Example 12 | <1 |
| Example 13 | <1 |
| Example 25 | <1 |
| Example 27 | <1 |
| Example 30 | <1 |

The inhibition activity of the typical compounds represented by Chemical Formula 1 against various kinases is as follows. The kinase activity inhibition data were obtained using Millipore's KinaseProfiler™. Table 3 shows the kinase inhibition activity (% inhibition) of the compounds at a given concentration (1 µM).

TABLE 3

| Kinases | Kinase inhibition activity (% inhibition) at given concentration (1 µM) |
|---|---|
| ALK(h) | 67 |
| Aurora-A(h) | 100 |
| cKit(D816V)(h) | 81 |
| cSRC(h) | 92 |
| EphA1(h) | 94 |
| Flt3(D835Y)(h) | 91 |
| Fms(h) | 95 |
| Itk(h) | 94 |
| KDR(h) | 96 |
| Met(h) | 78 |
| Ret(h) | 96 |
| Syk(h) | 94 |
| Tie2(h) | 98 |
| TrkB(h) | 97 |

INDUSTRIAL APPLICABILITY

As described, since the 2,7-substituted thieno[3,2-d]pyrimidine compound represented by Chemical Formula 1 or a pharmaceutically acceptable exhibits inhibition activity against protein kinases, it is useful for preventing and treating diseases caused by abnormal cell growth induced by protein kinases, such as tumors selected from stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma and fibroadenoma.

The present application contains subject matter related to Korean Patent Application No. 10-2009-0100867, filed in the Korean Intellectual Property Office on Oct. 22, 2009, the entire contents of which is incorporated herein by reference.

While the present invention has been described with respect to the specific embodiments, it will be apparent to those skilled in the art that various changes and modifications may be made without departing from the spirit and scope of the invention as defined in the following claims.

The invention claimed is:

1. A compound represented by Chemical Formula 1 or a pharmaceutically acceptable salt thereof:

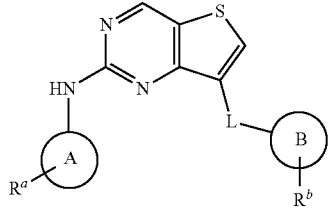

[Chemical Formula 1]

wherein

A represents 5- to 14-membered heteroaryl containing 1 to 4 heteroatom(s) selected from nitrogen, oxygen and sulfur atoms;

$R^a$ represents hydrogen, halogen, oxo (=O), $C_1$-$C_6$ alkyl, $C_1$-$C_6$ alkoxy, $C_1$-$C_6$ alkylcarbonyl, $C_1$-$C_6$ alkoxycarbonyl, amino $C_1$-$C_6$ alkoxy, mono($C_1$-$C_6$ alkyl)amino $C_1$-$C_6$ alkoxy, di($C_1$-$C_6$ alkyl)amino $C_1$-$C_6$ alkoxy, substituted or unsubstituted heterocycle, or substituted or unsubstituted phenyl;

L is nonexistent or represents —NH— or —N($C_1$-$C_6$ alkyl)—;

B represents phenyl or 5- to 14-membered single or fused heteroaryl containing 1 to 4 heteroatom(s) selected from nitrogen, oxygen and sulfur atoms;

$R^b$ represents hydrogen, nitro, amino, hydroxy, $C_1$-$C_6$ haloalkyl, $C_1$-$C_6$ alkoxy, —(CH$_2$)$_n$—R$^1$, —C(O)OR$^2$, —C(O)NR$^3$R$^4$, —NR$^2$C(O)R$^3$, —NR$^2$C(O)NR$^3$R$^4$, —SO$_2$NR$^3$R$^4$ or —NR$^2$SO$_2$R$^3$;

n represents an integer from 0 to 3;

$R^1$ represents hydrogen, $C_1$-$C_6$ alkyl, haloalkyl, hydroxy, methanesulfonyl, phenyl, or substituted or unsubstituted heterocycle;

$R^2$ represents hydrogen or $C_1$-$C_6$ alkyl;

$R^3$ and $R^4$, which are the same or different, represent hydrogen, $C_1$-$C_6$ alkyl, $C_3$-$C_6$ cycloalkyl, $C_1$-$C_6$ haloalkyl, or substituted or unsubstituted phenyl;

the substituted phenyl is substituted with a substituent selected from halogen, $C_1$-$C_6$ haloalkyl, carboxyl and $C_1$-$C_6$ alkoxycarbonyl; and the substituted heterocycle represents morpholino, piperidinyl or piperazinyl substituted with a substituent selected from $C_1$-$C_6$ alkyl and $C_1$-$C_6$ hydroxyalkyl.

2. The compound according to claim 1, wherein

A represents heteroaryl selected from thiophenyl, thiazolyl, thiadiazolyl, tetrazolyl, pyridinyl, pyrimidinyl, pyrazinyl, naphthridinyl, benzoimidazolyl, benzothiazolyl, quinazolinyl and dihydroquinazolinyl;

$R^a$ represents hydrogen, halogen, oxo (=O), $C_1$-$C_6$ alkyl, $C_1$-$C_6$ alkylcarbonyl, $C_1$-$C_6$ alkoxycarbonyl, amino $C_1$-$C_6$ alkoxy, mono($C_1$-$C_6$ alkyl)amino $C_1$-$C_6$ alkoxy, di($C_1$-$C_6$ alkyl)amino $C_1$-$C_6$ alkoxy, morpholino, piperazinyl, 4-($C_1$-$C_6$ alkyl)piperazinyl, 4-($C_1$-$C_6$ hydroxyalkyl)piperazinyl, or substituted or unsubstituted phenyl;

L is nonexistent or represents —NH— or —N($C_1$-$C_6$ alkyl)—;

B represents phenyl or quinolinyl;

$R^b$ represents hydrogen, $C_1$-$C_6$ haloalkyl, $C_1$-$C_6$ alkoxy, —(CH$_2$)$_n$—R$^1$, —C(O)NR$^3$R$^4$, —NR$^2$C(O)R$^3$, —NR$^2$C(O)NR$^3$R$^4$, —SO$_2$NR$^3$R$^4$ or —NR$^2$SO$_2$R$^3$;

n represents an integer from 0 to 3;

$R^1$ represents hydrogen, 1,1-dioxidoisothiadiazolidinyl, morpholino, piperidinyl, piperazinyl or 4-($C_1$-$C_6$ alkyl)piperazinyl;

$R^2$ represents hydrogen or $C_1$-$C_6$ alkyl;

$R^3$ and $R^4$, which are the same or different, represent hydrogen, $C_1$-$C_6$ alkyl, $C_3$-$C_6$ cycloalkyl, $C_1$-$C_6$ haloalkyl, or substituted or unsubstituted phenyl; and the substituted phenyl is substituted with a substituent selected from halogen, $C_1$-$C_6$ haloalkyl, carboxyl and $C_1$-$C_6$ alkoxycarbonyl.

3. The compound according to claim 1, wherein

A represents pyridinyl;

$R^a$ represents methyl, ethyl, morpholino, dimethylaminoethoxy, 4-ethylpiperazinyl or 4-(2-hydroxyethyl)piperazinyl;

L is nonexistent;

B represents phenyl or quinolinyl; and $R^b$ represents hydrogen, —NHSO$_2$CH$_3$ or —C(O)NH-cyclopropyl.

4. A compound, which is selected from the group consisting of:

N-(3-(2-(6-(4-ethylpiperazin-1-yl)pyridin-3-ylamino)thieno[3,2-d]pyrimidin-7-yl)phenyl)methanesulfonamide;

N-(3-(2-(1H-tetrazol-5-ylamino)thieno[3,2-d]pyrimidin-7-yl)phenyl)methanesulfonamide;

N-(3-(2-(6-fluorobenzo[d]thiazol-2-ylamino)thieno[3,2-d]pyrimidin-7-yl)phenyl)methanesulfonamide;

N-(3-(2-(4,5-dimethylthiazol-2-ylamino)thieno[3,2-d]pyrimidin-7-yl)phenyl)methanesulfonamide;

N-(3-(2-(5-phenyl-1,3,4-thiadiazol-2-ylamino)thieno[3,2-d]pyrimidin-7-yl)phenyl)methanesulfonamide;

N-(3-(2-(4-phenylthiazol-2-ylamino)thieno[3,2-d]pyrimidin-7-yl)phenyl)methanesulfonamide;

N-(3-(2-(pyrazin-2-ylamino)thieno[3,2-d]pyrimidin-7-yl)phenyl)methanesulfonamide;

N-(3-(2-(3H-benzo[d]imidazol-5-ylamino)thieno[3,2-d]pyrimidin-7-yl)phenyl)methanesulfonamide;

N-(3-(2-(5,7-dimethyl-1,8-naphthyridin-2-ylamino)thieno[3,2-d]pyrimidin-7-yl)phenyl)methanesulfonamide;

N-(3-(2-(6-methylbenzo[d]thiazol-2-ylamino)thieno[3,2-d]pyrimidin-7-yl)phenyl)methanesulfonamide;

N-(3-(2-(6-methylpyridin-3-ylamino)thieno[3,2-d]pyrimidin-7-yl)phenyl)methanesulfonamide;
N-(3-(2-(6-morpholinopyridin-3-ylamino)thieno[3,2-d]pyrimidin-7-yl)phenyl)methanesulfonamide;
N-(3-(2-(6-(2-(dimethylamino)ethoxy)pyridin-3-ylamino)thieno[3,2-d]pyrimidin-7-yl)phenyl)methanesulfonamide;
ethyl 3-(5-(7-(3-(methylsulfonamido)phenyl)thieno[3,2-d]pyrimidin-2-ylamino)pyridin-2-yl)benzoate;
ethyl 4-(5-(7-(3-(methylsulfonamido)phenyl)thieno[3,2-d]pyrimidin-2-ylamino)pyridin-2-yl)benzoate;
ethyl 5-(7-(3-(methylsulfonamido)phenyl)thieno[3,2-d]pyrimidin-2-ylamino)nicotinate;
N-(3-(2-(6-morpholinopyrimidin-4-ylamino)thieno[3,2-d]pyrimidin-7-yl)phenyl)methanesulfonamide;
N-(3-(2-(6-(4-ethylpiperazin-1-yl)pyrimidin-4-ylamino)thieno[3,2-d]pyridin-7-yl)phenyl)methanesulfonamide;
N-(3-(2-(6-(4-hydroxyethylpiperazin-1-yl)pyridin-3-ylamino)thieno[3,2-d]pyrimidin-7-yl)phenyl)methanesulfonamide;
N-(3-(2-(3-methyl-4-oxo-3,4-dihydroquinazolin-7-ylamino)thieno[3,2-d]pyrimidin-7-yl)phenyl)methanesulfonamide;
N-(3-(2-(5-acetylthiophen-2-ylamino)thieno[3,2-d]pyrimidin-7-yl)phenyl)methanesulfonamide;
7-(4-((4-ethylpiperazin-1-yl)methyl)phenyl)-N-(6-morpholinopyridin-3-yl)thieno[3,2-d]pyridin-2-amine;
N-(6-morpholinopyridin-3-yl)-7-(4-(piperidin-1-ylmethyl)phenyl)thieno[3,2-d]pyrimidin-2-amine;
7-(4-(morpholinomethyl)phenyl)-N-(6-morpholinopyridin-3-yl)thieno[3,2-d]pyrimidin-2-amine;
N-cyclopropyl-3-(2-(6-(4-ethylpiperazin-1-yl)pyridin-3-ylamino)thieno[3,2-d]pyrimidin-7-yl)benzamide;
N-cyclopropyl-3-(2-(6-methylpyridin-3-ylamino)thieno[3,2-d]pyrimidin-7-yl)benzamide;
N-cyclopropyl-3-(2-(6-morpholinopyridin-3-ylamino)thieno[3,2-d]pyrimidin-7-yl)benzamide;
N-cyclopropyl-3-(2-(6-(4-(2-hydroxyethyl)piperazin-1-yl)-2-methylpyrimidin-4-ylamino)thieno[3,2-d]pyrimidin-7-yl)benzamide;
3-(2-(6-(4-(2-hydroxyethyl)piperazin-1-yl)-2-methylpyrimidin-4-ylamino)thieno[3,2-d]pyrimidin-7-yl)-N-methylbenzenesulfonamide;
N-(6-(4-ethylpiperazin-1-yl)pyridin-3-yl)-7-(quinolin-3-yl)thieno[3,2-d]pyrimidin-2-amine;
N-(6-methylpyridin-3-yl)-7-(quinolin-3-yl)thieno[3,2-d]pyrimidin-2-amine;
N-(6-morpholinopyridin-3-yl)-7-(quinolin-3-yl)thieno[3,2-d]pyrimidin-2-amine;
N-(3-(2-(6-morpholinopyridin-3-ylamino)thieno[3,2-d]pyrimidin-7-yl)phenyl)cyclopropanecarboxamide;
N-(3-(2-(6-morpholinopyridin-3-ylamino)thieno[3,2-d]pyrimidin-7-yl)phenyl)acetamide;
N-(3-(2-(1H-tetrazol-5-ylamino)thieno[3,2-d]pyrimidin-7-yl)phenyl)methanesulfonamide;
N-(3-(2-(6-morpholinopyridin-3-ylamino)thieno[3,2-d]pyrimidin-7-yl)phenyl)isopropylcarboxamide;
4-chloro-N-(3-(2-(6-morpholinopyridin-3-ylamino)thieno[3,2-d]pyrimidin-7-yl)phenyl)-3-(trifluoromethyl)benzamide;
N-(3-(2-(6-morpholinopyridin-3-ylamino)thieno[3,2-d]pyrimidin-7-yl)phenyl)ethanesulfonamide;
N-(3-(2-(6-morpholinopyridin-3-ylamino)thieno[3,2-d]pyrimidin-7-yl)phenyl)cyclopropanesulfonamide;
1-(4-chloro-3-(trifluoromethyl)phenyl)-3-(3-(2-(6-morpholinopyridin-3-ylamino)thieno[3,2-d]pyrimidin-7-yl)phenyl)urea;
1-cyclohexyl-3-(3-(2-(6-morpholinopyridin-3-ylamino)thieno[3,2-d]pyrimidin-7-yl)phenyl)urea;
1-(3-(2-(6-morpholinopyridin-3-ylamino)thieno[3,2-d]pyrimidin-7-yl)phenyl)-3-(2,2,2-trifluoroethyl)urea;
N-(6-(4-ethylpiperazin-1-yl)pyridin-3-yl)-7-(2-(trifluoromethyl)phenyl)thieno[3,2-d]pyrimidin-2-amine;
N-(6-morpholinopyridin-3-yl)-7-(2-(trifluoromethyl)phenyl)thieno[3,2-d]pyrimidin-2-amine;
N-(3-(2-(6-(4-ethylpiperazin-1-yl)pyridin-3-ylamino)thieno[3,2-d]pyrimidin-7-yl)phenyl)-N-methylmethanesulfonamide;
N-methyl-N-(3-(2-(6-methylpyridin-3-ylamino)thieno[3,2-d]pyrimidin-7-yl)phenyl)methanesulfonamide;
N-methyl-N-(3-(2-(6-morpholinopyridin-3-ylamino)thieno[3,2-d]pyrimidin-7-yl)phenyl)methanesulfonamide;
$N^2$-(6-morpholinopyridin-3-yl)-$N^7$-(3,4,5-trimethoxyphenyl)thieno[3,2-d]pyrimidin-2,7-diamine;
$N^7$-methyl-$N^2$-(6-morpholinopyridin-3-yl)-$N^7$-(3,4,5-trimethoxyphenyl)thieno[3,2-d]pyrimidin-2,7-diamine;
7-(3-(1,1-dioxido-2-isothiadiazolidinyl)phenyl)-N-(6-(4-ethylpiperazin-1-yl)pyridin-3-yl)thieno[3,2-d]pyrimidin-2-amine; and
N-(3-(2-(6-(4-ethylpiperazin-1-yl)pyridin-3-ylamino)thieno[3,2-d]pyrimidin-7-yl)phenyl)methanesulfonamide hydrochloride.

5. A pharmaceutical composition comprising the compound according to claim 1 as an effective ingredient and a pharmaceutically acceptable carrier.

6. A method for preparing a compound represented by Chemical Formula 1 according to claim 1, comprising:
subjecting a 7-bromo-2-chlorothieno[3,2-d]pyrimidine compound represented by Chemical Formula 2 to Suzuki coupling reaction with a boronic acid compound or Buchwald amination reaction represented by Chemical Formula 3 to prepare a compound represented by Chemical Formula 4 with a group B introduced at the C-7 position:

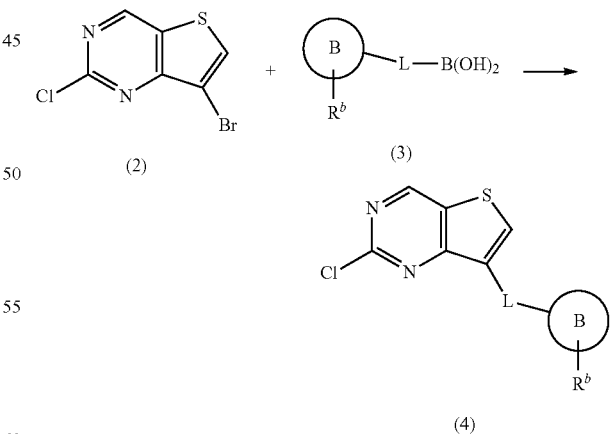

(wherein A, B, $R^a$ and $R^b$ are the same as defined in claim 1); and
subjecting the compound represented by Chemical Formula 4 to Buchwald amination reaction with an amine compound represented by Chemical Formula 5 to prepare the compound represented by Chemical Formula 1:

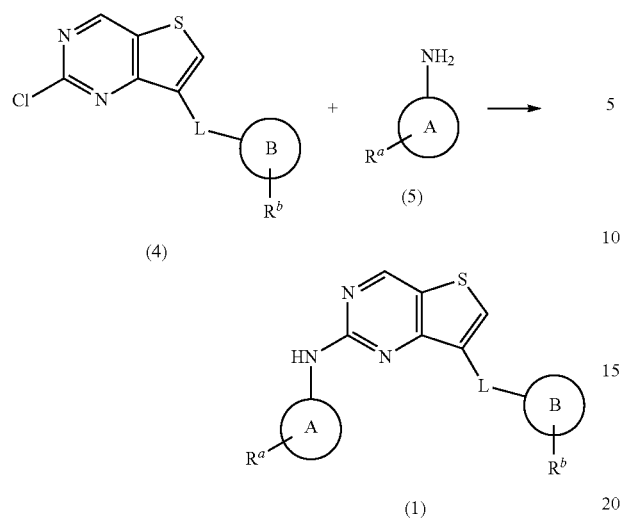
(wherein A, B, $R^a$ and $R^b$ are the same as defined in claim 1).
7. The preparation method according to claim 6, wherein the Suzuki coupling reaction or the Buchwald amination reaction is performed in the presence of a metal catalyst selected from $Pd_2(dba)_3$, $Pd(OAc)_2$, $PdCl_2(PPh_3)_2$ and $Pd(PPh_3)_4$.
* * * * *